United States Patent
Schütz et al.

(10) Patent No.: US 7,538,118 B2
(45) Date of Patent: May 26, 2009

(54) 6-AMINOMORPHINANE DERIVATIVES, METHOD FOR PRODUCTION AND USE THEREOF

(75) Inventors: Johannes Schütz, Innsbruck (AT); Helmut Schmidhammer, Innsbruck (AT)

(73) Assignee: Alcasynn Pharmaceuticals GmbH, Innsbruck (AT)

( * ) Notice: Subject to any disclaimer, the term of this patent is extended or adjusted under 35 U.S.C. 154(b) by 633 days.

(21) Appl. No.: 10/499,133

(22) PCT Filed: Dec. 16, 2002

(86) PCT No.: PCT/EP02/14343

§ 371 (c)(1), (2), (4) Date: Sep. 21, 2004

(87) PCT Pub. No.: WO03/051888

PCT Pub. Date: Jun. 26, 2003

(65) Prior Publication Data

US 2005/0038061 A1     Feb. 17, 2005

(30) Foreign Application Priority Data

Dec. 17, 2001    (DE)  ................. 101 61 963

(51) Int. Cl.
*A61K 31/485*    (2006.01)
*C07D 489/08*    (2006.01)

(52) U.S. Cl. ............... 514/282; 546/44; 546/46

(58) Field of Classification Search ......... 514/282; 546/44, 46

See application file for complete search history.

(56) References Cited

U.S. PATENT DOCUMENTS

| | | | |
|---|---|---|---|
| 4,806,556 A | * | 2/1989 | Portoghese ............... 546/44 |
| 4,912,114 A | | 3/1990 | Revesz |
| 6,469,030 B2 | * | 10/2002 | Farrar et al. ............. 514/331 |
| 2001/0036951 A1 | | 11/2001 | Farrar et al. |

FOREIGN PATENT DOCUMENTS

| | | |
|---|---|---|
| WO | WO 95/03307 | 2/1995 |
| WO | WO 95/03308 | 2/1995 |
| WO | WO 01/68080 | 9/2001 |

OTHER PUBLICATIONS

"Synthesis of 14-alkoxymorphinan-6-ones (starting from Naltrexon) as Potential δopioid Receptor Antagonists", Thesis for the Degree of Ph.D. in Natural Sciences of the Leopold-Franzens University of Innsbruck, Submitted by Mag. Pharm. Roland Krassnig, Innsbruck 1994.

* cited by examiner

*Primary Examiner*—Charanjit S Aulakh
(74) *Attorney, Agent, or Firm*—Cohen Pontani Lieberman & Pavane LLP

(57) ABSTRACT

This invention relates to compounds of the formula (I).

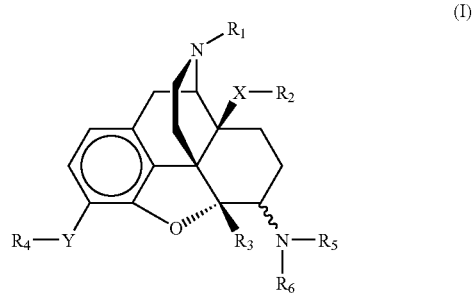

7 Claims, No Drawings

6-AMINOMORPHINANE DERIVATIVES, METHOD FOR PRODUCTION AND USE THEREOF

PRIORITY CLAIM

This is a U.S. national stage of application No. PCT/EP02/14343, filed on 16 Dec. 2002. Priority is claimed on that application and on the following application(s): Country: Germany, Application No.: 101 61 963.4, Filed: 17 Dec. 2001.

This invention relates to a class of 6-amino-morphinan compounds which can be used as highly active analgesics. This invention also relates to their pharmaceutically acceptable salts and easily accessible derivatives (e.g. esters or amides of the amino acid derivatives), to a process for their manufacture and their application in the manufacture of pharmaceutical specialities.

BACKGROUND OF THE INVENTION

The existence of opioid receptors as receptors of the central nervous system (CNS), which transfer an analgesic effect, has been clearly proven. These receptors are subdivided into three subtypes, μ, κ and δ. Activation of these receptors by opioids results in an analgesic effect. The activation of the μ receptors causes the highest analgesic effect, whereby particularly morphinans with an oxygen function in position 6 (morphine, oxymorphone, hydromorphone, etc.) are used as effective analgesics. In the past a great deal of work has been invested in the structure-activity relationship studies of this class of substance.

In the Journal of Medicinal Chemistry 1984, 27, pp. 1575-1579 various 14-methoxymorphinan-6-ones with various substituents in position 3 are described. These derivatives exhibit higher analgesic activity than their 14-hydroxy counterparts.

A detailed study of 5-methyloxymorphone (=14-hydroxy-5-methyldihydromorphinone) is described in Helvetica Chimica Acta (1988, 71, pp. 1801-1804) which arrives at the result that the introduction of a 5-methyl group reduces the opioid agonistic characteristics of oxymorphone.

A further study on 14-alkoxymorphinan-6-ones is described in Helvetica Chimica Acta 1989, 72, pp. 1233-1239 in which the influence of various substituents in position 3 and of the amino nitrogen was evaluated.

The German disclosure document DE 34 12 727 describes 14-alkoxy-N-methylmorphinan-6-ones (14-O-alkyloxymorphone) with higher activity than their 14-hydroxy counterparts.

Recently the existence of opioid receptors in the periphery has also been detected (e.g. in bones, joints, cartilage, muscles, etc.). It could be shown that analgesia is also imparted via these peripheral opioid receptors (C. Stein, New Engl. J. Med. 1995, 332, pp. 1685-1690). For this, only a slight dose of an opioid (e.g. morphine), which is applied directly into the injured tissue by injection, is necessary. This slight dose does not result in any side effects being imparted by the central nervous system. The analgesic effect has been observed especially during the treatment of inflammation and neuropathic pain (R. Likar et al., Brit. J. Anaesth. 1999, 83, pp. 241-244; V. Kayser et al., Neurosci. 1995, 64, 537-545). The type of application (injection) represents a significant disadvantage of the treatment. Repeated injections into the affected tissue or joint are associated with risks such as bleeding, infections or cartilage damage. Analgesically effective substances, which have only a limited access to the central nervous system (due to the fact that they cannot pass, or pass only to a very small extent, the blood-brain barrier) and which can be administered systemically or orally, are of great interest.

SUMMARY OF THE INVENTION

The object of this invention was to produce highly active analgesics which preferably possess restricted access to the CNS and which preferably act peripherally and not centrally and which also can be preferably systemically or orally administered. Substances showing promise of success in this connection would be ones which indicate an exclusively peripheral analgesic effect, without the side effects which occur with a centrally acting effect.

This invention solves the object presented above through the object of the independent claims. Preferred embodiments are given in the subclaims.

This invention provides highly active compounds of the formula (I),

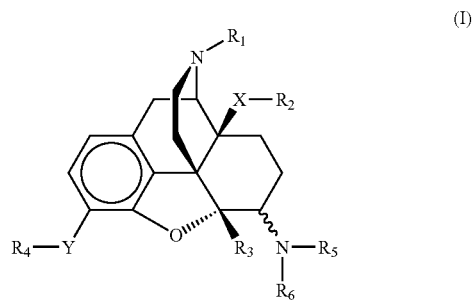

(I)

in which the substituents have the following meaning:

$R_1$: hydrogen; $C_1$-$C_6$-alkyl; $C_2$-$C_6$-alkenyl; $C_2$-$C_6$-alkinyl; $C_1$-$C_6$-monohydroxyalkyl; $C_2$-$C_6$-dihydroxyalkyl; $C_3$-$C_6$-trihydroxyalkyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl.

The nitrogen joined with $R_1$ can also be quarternised by two substituents $R_1$, which can be the same or different and which are defined as previously shown, and where the second, quarternising substituent can also have the meaning hydroxyl, oxyl (N oxide) as well as alkoxyl.

$R_2$, subject to the following definition of X: hydrogen; $C_1$-$C_6$-alkyl; $C_2$-$C_6$-alkenyl; $C_2$-$C_6$-alkinyl; $C_1$-$C_6$-monohydroxyalkyl; $C_2$-$C_6$-dihydroxyalkyl; $C_3$-$C_6$-trihydroxyalkyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl; $C_2$-$C_6$-alkanoyl; $C_3$-$C_6$-alkenoyl; $C_3$-$C_6$-alkinoyl;

$C_7$-$C_{16}$-arylalkanoyl, where aryl is $C_6$-$C_{10}$-aryl and alkanoyl is $C_1$-$C_6$-alkanoyl; $C_9$-$C_{16}$-arylalkenoyl, where aryl is $C_6$-$C_{10}$-aryl and alkenoyl is $C_3$-$C_6$-alkenoyl; $C_9$-$C_{16}$-arylalkinoyl, where aryl is $C_6$-$C_{10}$-aryl and alkinoyl is $C_3$-$C_6$-alkinoyl.

$R_3$: hydrogen; $C_1$-$C_6$-alkyl; $C_2$-$C_6$-alkenyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; alkoxyalkyl, where alkoxy is $C_1$-$C_6$-alkoxy and alkyl is $C_1$-$C_6$-alkyl; $CO_2(C_1$-$C_6$-alkyl); $CO_2H$; $CH_2OH$.

$R_4$, subject to the following definition of Y: hydrogen; $C_1$-$C_6$-alkyl; $C_2$-$C_6$-alkenyl; $C_2$-$C_6$-alkinyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl; $C_2$-$C_6$-alkanoyl; $C_3$-$C_6$-alkenoyl; $C_3$-$C_6$-alkinoyl; $C_7$-$C_{16}$-arylalkanoyl, where aryl is $C_6$-$C_{10}$-aryl and alkanoyl is $C_1$-$C_6$-alkanoyl; $C_9$-$C_{16}$-arylalkenoyl, where aryl is $C_6$-$C_{10}$-aryl and alkenoyl is $C_3$-$C_6$-alkenoyl; $C_9$-$C_{16}$-arylalkinoyl, where aryl is $C_6$-$C_{10}$-aryl and alkinoyl is $C_3$-$C_6$-alkinoyl; iminomethyl, formamidinyl, $C_1$-$C_6$—N-alkyl- and N,N'-dialkylformamidinyl; $C_2$-$C_6$—N-alkenyl- and N,N'-dialkenylformamidinyl; $C_2$-$C_6$—N-alkinyl- and N,N'-dialkinylformamidinyl; $C_4$-$C_{16}$—N-cycloalkylalkyl- and N,N'-dicycloalkylalkylformamidinyl, where cycloalkyl is $C_3$-$C_{10}$-cycloalkyl and alkyl is $C_1$-$C_6$-alkyl; $C_5$-$C_{16}$—N-cylcoalkylalkenyl- and N,N'-dicycloalkylalkenylformamidinyl, where cycloalkyl is $C_3$-$C_{10}$-cycloalkyl and alkenyl is $C_2$-$C_6$-alkenyl; $C_5$-$C_{16}$—N-cycloalkylalkinyl- and N,N'-dicycloalkylalkinylformamidinyl, where cycloalkyl is $C_3$-$C_{10}$-cycloalkyl and alkinyl is $C_2$-$C_6$-alkinyl; $C_7$-$C_{16}$—N-arylalkyl- and N,N'-diarylalkylformamidinyl, where aryl is $C_6$-$C_{10}$-aryl and alkyl is $C_1$-$C_6$-alkyl.

$R_5$ and $R_6$, which can be the same or different: hydrogen; $C_1$-$C_6$-alkyl; $C_2$-$C_6$-alkenyl; $C_2$-$C_6$-alkinyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl; furthermore, $R_5$ and $R_6$, which can be the same or different, $CH(A)CO_2B$, where A is hydrogen; hydroxyl; $C_1$-$C_6$-alkyl; $C_2$-$C_6$-alkenyl; $C_2$-$C_6$-alkinyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl; amino; $C_1$-$C_6$-alkylamino; guanidino; $C_1$-$C_6$-alkyl-$CO_2B$; and where B is hydrogen; $C_1$-$C_{30}$-, preferably $C_1$-$C_6$-alkyl; $C_2$-$C_{30}$-, preferably $C_2$-$C_6$-alkenyl; $C_2$-$C_{30}$-, preferably $C_2$-$C_6$-alkinyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl; phenyl; substituted phenyl; $CH_2OCO$—$C_1$-$C_6$-alkyl; $CH(C_1$-$C_6$-alkyl)$OCO$—$C_1$-$C_6$-alkyl; $CH_2OCOO$—$C_1$-$C_6$-alkyl; $CH(C_1$-$C_6$-alkyl)$OCOO$—$C_1$-$C_6$-alkyl; $CH_2CON(C_1$-$C_6$-alkyl)$_2$; $CH(C_1$-$C_6$-alkyl)$CON(C_1$-$C_6$-alkyl)$_2$; phthalidyl, (5-methyl-2-oxo-1,3-dioxol-4-yl)methyl; furthermore $CH(A)SO_3B$, where A and B are defined as above; also $R_5$ and $R_6$, which can be the same or different, can represent iminomethyl, formamidinyl, $C_1$-$C_6$—N-alkyl- and N,N'-dialkylformamidinyl; $C_2$-$C_6$—N-alkenyl- and N,N'-dialkenylformamidinyl; $C_2$-$C_6$—N-alkinyl- and N,N'-dialkinylformamidinyl; $C_4$-$C_{16}$—N-cycloalkylalkyl- and N,N'-dicycloalkylalkylformamidinyl, where cycloalkyl is $C_3$-$C_{10}$-cycloalkyl and alkyl is $C_1$-$C_6$-alkyl; $C_3$-$C_{16}$—N-cylcoalkylalkenyl- and N,N'-dicycloalkylalkenylformamidinyl, where cycloalkyl is $C_3$-$C_{10}$-cycloalkyl and alkenyl is $C_2$-$C_6$-alkenyl; $C_5$-$C_{16}$—N-cycloalkylalkinyl- and N,N'-dicycloalkylalkinylformamidinyl, where cycloalkyl is $C_3$-$C_{10}$-cycloalkyl and alkinyl is $C_2$-$C_6$-alkinyl; $C_7$-$C_{16}$—N-arylalkyl- and N,N'-diarylalkylformamidinyl, where aryl is $C_6$-$C_{10}$-aryl and alkyl is $C_1$-$C_6$-alkyl; $C_8$-$C_{16}$—N-arylalkenyl- and N,N'-diarylalkenylformamidinyl, where aryl is $C_6$-$C_{10}$-aryl and alkenyl is $C_2$-$C_6$-alkenyl; $C_8$-$C_{16}$—N-arylalkinyl- and N,N'-diarylalkinylformamidinyl, where aryl is $C_6$-$C_{10}$-aryl and alkinyl is $C_2$-$C_6$-alkinyl; $C_2$-$C_7$—N-alkyloxycarbonyl- and N,N'-bis(alkyloxycarbonyl)formamidinyl; $C_3$-$C_8$—N-alkenyloxycarbonyl- and N,N'-bis(alkenyloxycarbonyl)formamidinyl; $C_3$-$C_8$—N-alkinyloxycarbonyl- and N,N'-bis(alkinyloxycarbonyl)formamidinyl; $C_8$-$C_{17}$—N-arylalkyloxycarbonyl- and N,N'-bis(arylalkyloxycarbonyl)formamidinyl, where aryl is $C_6$-$C_{10}$-aryl and alkyloxy is $C_1$-$C_6$-alkyloxy; $C_9$-$C_{17}$—N-arylalkenyloxycarbonyl- and N,N'-bis(arylalkenyloxycarbonyl)formamidinyl, where aryl is $C_6$-$C_{10}$-aryl and alkenyloxy is $C_2$-$C_6$-alkenyloxy; $C_9$-$C_{17}$—N-arylalkinyloxycarbonyl- and N,N'-bis(arylalkinyloxycarbonyl)formamidinyl, where aryl is $C_6$-$C_{10}$-aryl and alkinyloxy is $C_2$-$C_6$-alkinyloxy; $C_2$-$C_7$—N-alkanoyl- and N,N'-dialkanoylformamidinyl; $C_3$-$C_8$—N-alkenoyl- and N,N'-dialkenoylformamidinyl; $C_3$-$C_8$—N-alkinoyl- and N,N'-dialkinoylformamidinyl; $C_8$-$C_{16}$—N-arylalkanoyl- and N,N'-diarylalkanoylformamidinyl, where aryl is $C_6$-$C_{10}$-aryl and alkanoyl is $C_2$-$C_6$-alkanoyl; $C_9$-$C_{16}$—N-arylalkenoyl- and N,N'-diarylalkenoylformamidinyl, where aryl is $C_6$-$C_{10}$-aryl and alkenoyl is $C_3$-$C_6$-alkenoyl; $C_9$-$C_{16}$—N-arylalkinoyl- and N,N'-diarylalkinoylformamidinyl, where aryl is $C_6$-$C_{10}$-aryl and alkinoyl is $C_3$-$C_6$-alkinoyl; also $R_5$ and $R_6$, which can be the same or different, can be 4,5-dihydro-1H-imidazol-2-yl, 1,4,5,6-tetrahydropyrimidin-2-yl, 4,5,6,7-tetrahydro-1H-[1,3]diazepin-2-yl.

X is oxygen, sulphur or methylene or the group (X—$R_2$) is H.
Y is oxygen or the group (Y—$R_4$) is H.

This invention also includes pharmaceutically acceptable acid addition salts and easily accessible derivatives (e.g. esters or amides of the amino acid derivatives) of the compounds of formula (I).

In this invention the terms alkyl, alkenyl and alkinyl include both branched and also unbranched alkyl, alkenyl and alkinyl groups as well as mono-, di- and trihydroxy-substituted branched and unbranched alkyl, alkenyl and alkinyl groups. Aryl can be unsubstituted or mono-, di- or tri-substituted, whereby the substituents can be chosen independently from hydroxy, halogen, nitro, cyano, thiocyanato, trifluoromethyl, $C_1$-$C_3$-alkyl, $C_1$-$C_3$-alkoxy, $CO_2H$, $CONH_2$, $CO_2(C_1$-$C_3$-alkyl), $CONH(C_1$-$C_3$-alkyl), $CON(C_1$-$C_3$-alkyl)$_2$, $CO(C_1$-$C_3$-alkyl); amino; $(C_1$-$C_3$-monoalkyl)amino, $(C_1$-$C_3$-dialkyl)amino, $C_5$-$C_6$-cycloalkylamino; $(C_1$-$C_3$-alkanoyl) amido, SH, $SO_3H$, $SO_3(C_1$-$C_3$-alkyl), $SO_2(C_1$-$C_3$-alkyl), $SO(C_1$-$C_3$-alkyl), $C_1$-$C_3$-alkylthio or $C_1$-$C_3$-alkanoylthio. The definitions listed above for alkyl, alkenyl, alkinyl and aryl are valid for all substituents of this application.

The compounds of this invention contain pharmaceutically and pharmacologically acceptable salts of the compounds of formula (I). According to this invention both inorganic and also organic salts are suitable. Examples of suitable inorganic salts for this invention are hydrochlorides, hydrobromides, sulphates, phosphates and tetrafluoroborates. Possible organic salts are, for example, acetates, tartrates, lactates, benzoates, stearates, pamoates, methane sulphonates, salicylates, fumarates, maleinates, succinates, aspartates, citrates, oxalates, trifluoroacetates and orotates.

Acid addition salts are preferred as conventional pharmaceutically acceptable addition salts, particularly preferred are the hydrochlorides, hydrobromides, tetrafluoroborates and trifluoroacetates. X and Y are preferably oxygen. Preferably $R_1$ is alkyl as defined above, in particular methyl or ethyl, whereby methyl is preferred, or cycloalkylalkyl, preferably cyclopropylmethyl. $R_2$ is preferably not H and also not a group which forms an ester unit with X. The other definitions for $R_2$ as defined in Claim 1 are, in contrast, preferred, whereby especially alkyl as defined above is preferred, particularly preferred are methyl, ethyl and propyl, where necessary substituted, e.g. with a phenyl group, for example to produce a 3-phenylpropyl group (i.e., put differently, an arylalkyl group is also preferred for $R_2$, in particular 3-phenylpropyl). $R_1$ and $R_2$ are especially preferably both simultaneously alkyl, in particular either both simultaneously methyl or methyl ($R_1$) and ethyl ($R_2$). A further preferred combination of $R_1$ and $R_2$ is cycloalkylalkyl, in particular cyclopropylmethyl for $R_1$ and arylalkyl, preferably phenylpropyl for $R_2$. $R_3$ and $R_4$ are in each case preferably hydrogen or alkyl, whereby methyl is especially preferred as an alkyl group. $R_4$ is in addition preferred as C(N-Boc) (NH-Boc). $R_5$ and $R_6$ are preferably chosen such that one is H and the other is different to H, whereby this radical, different to H, is preferably not halogenated. $R_5$ and $R_6$ are preferably selected, independent of one another, from hydrogen, $CH_2COOC(CH_3)_3$, $CH_2COOH$, $CH(CH_3)COOC(CH_3)$, $CH(CH_3)COOH$, $CH(CH_2Ph)COOC(CH_3)_3$, $CH(CH_2Ph)COOH$, C(N-Boc) NH-BOC and $C(NH)NH_2$, whereby $R_6$ is preferably H and $R_5$ is preferably one of the groups mentioned above or is H. Also preferred, $R_5$ and $R_6$ are both H.

In a specially preferred representation X and Y are oxygen. Then preferably, $R_1$ is methyl and cyclopropylmethyl and $R_2$ is alkyl and arylalkyl, in particular methyl and 3-phenylpropyl, and $R_3$, $R_4$ and $R_6$ are hydrogen. Preferably, $R_5$ is then chosen as tert.-butoxycarbonylmethyl, hydroxycarbonylmethyl, 2-(tert.-butoxycarbonylethyl), 2-(hydroxycarbonylethyl), 2-(tert.-butoxycarbonyl-1-phenylethyl), 2-(hydroxycarbonyl-2-phenylethyl), hydrogen, benzyl (in this case $R_6$ is also a benzyl group), N,N'-bis-(tert.-butoxycarbonyl)formamidinyl and formamidinyl.

In a particularly preferred representation of this invention the compound of the formula I is selected from:
(4,5α-epoxy-3-hydroxy-14β-methoxy-17-methylmorphinan-6α-ylamino)-acetic acid-tert.-butylester
(4,5α-epoxy-3-hydroxy-14β-methoxy-17-methylmorphinan-6β-ylamino)-acetic acid-tert.-butylester
(4,5α-epoxy-3-hydroxy-14β-methoxy-17-methylmorphinan-6α-ylamino)-acetic acid
(4,5α-epoxy-3-hydroxy-14β-methoxy-17-methylmorphinan-6β-ylamino)-acetic acid
(2'S)-2'-(4,5α-epoxy-3-hydroxy-14β-methoxy-17-methylmorphinan-6α-ylamino)-propionic acid-tert.-butylester
(2'S)-2'-(4,5α-epoxy-3-hydroxy-14β-methoxy-17-methylmorphinan-6β-ylamino)-propionic acid-tert.-butylester
(2'S)-2'-(4,5α-epoxy-3-hydroxy-14β-methoxy-17-methylmorphinan-6α-ylamino)-propionic acid
(2'S)-2'-(4,5α-epoxy-3-hydroxy-14β-methoxy-17-methylmorphinan-6β-ylamino)-propionic acid
(2'S)-2'-(4,5α-epoxy-3-hydroxy-14β-methoxy-17-methylmorphinan-6α-ylamino)-3'-phenylpropionic acid-tert.-butylester
(2'S)-2'-(4,5α-epoxy-3-hydroxy-14β-methoxy-17-methylmorphinan-6β-ylamino)-3'-phenylpropionic acid-tert.-butylester
(2'S)-2'-(4,5α-epoxy-3-hydroxy-14β-methoxy-17-methylmorphinan-6α-ylamino)-3'-phenylpropionic acid
(2'S)-2'-(4,5α-epoxy-3-hydroxy-14β-methoxy-17-methylmorphinan-6β-ylamino)-3'-phenylpropionic acid
6α-amino-4,5α-epoxy-14β-methoxy-17-methylmorphinan-3-ol
6β-dibenzylamino-4,5α-epoxy-14β-methoxy-17-methylmorphinan-3-ol
6β-amino-4,5α-epoxy-14β-methoxy-17-methylmorphinan-3-ol
4,5α-epoxy-6β-[N,N'-bis-(tert.-butoxycarbonyl)guanidinyl]-14β-methoxy-17-methylmorphinan-3-ol
4,5α-epoxy-6β-guanidinyl-14β-methoxy-17-methylmorphinan-3-ol
4,5α-epoxy-6α-[N,N'-bis-(tert.-butoxycarbonyl)guanidinyl]-14β-methoxy-17-methylmorphinan-3-ol
4,5α-epoxy-6α-guanidinyl-14β-methoxy-17-methylmorphinan-3-ol
1,3-bis-(tert.-butoxycarbonyl)-2-{4,5α-epoxy-6β-[N,N'-bis-(tert.-butoxycarbonyl)guanidinyl]-14β-methoxy-17-methylmorphinan-3-yl}-isourea
1,3-bis-(tert.-butoxycarbonyl)-2-{4,5α-epoxy-6α-[N,N'-bis-(tert.-butoxycarbonyl)guanidinyl]-14β-methoxy17-methylmorphinan-3-yl}-isourea
(4,5α-epoxy-3-hydroxy-14β-methoxy-17-methylmorphinan-6α-ylamino)-acetic acid-ethylester dihydrochloride
(4,5α-epoxy-3-hydroxy-14β-methoxy-17-methylmorphinan-6β-ylamino)-acetic acid-ethylester dihydrochloride
(4,5α-epoxy-3-hydroxy-14β-ethoxy-17-methylmorphinan-6α-ylamino)-acetic acid-tert.-butylester
(4,5α-epoxy-3-hydroxy-14β-ethoxy-17-methylmorphinan-6β-ylamino)-acetic acid-tert.-butylester
(4,5α-epoxy-3-hydroxy-14β-ethoxy-17-methylmorphinan-6α-ylamino)-acetic acid bis(tetrafluoroborate)
(4,5α-epoxy-3-hydroxy-14β-ethoxy-17-methylmorphinan-6β-ylamino)-acetic acid bis(tetrafluoroborate)
(2'S)-2'-(17-cyclopropylmethyl-4,5α-epoxy-3,14β-dihydroxymorphinan-6β-ylamino)-3-phenyl-propionic acid-tert.-butylester
(2'S)-2'-(17-cyclopropylmethyl-4,5α-epoxy-3,14β-dihydroxymorphinan-6β-ylamino)-3-phenyl-propionic acid bis(tetrafluoroborate)
{17-cyclopropylmethyl-4,5α-epoxy-3-hydroxy-14β-[(3-phenylpropyl)oxy]-morphinan-6α-ylamino}-acetic acid-tert.-butylester {17-cyclopropylmethyl-4,5α-epoxy-3-hydroxy-14β-[(3-phenylpropyl)oxy]-morphinan-6α-ylamino}-acetic acid-tert.-butylester
(2'S)-2'-(17-cyclopropylmethyl-4,5α-epoxy-3-hydroxy-14β-[(3-phenylpropyl)oxy]-morphinan-6α-ylamino)-3-phenylpropionic acid-tert.-butylester
{17-cyclopropylmethyl-4,5α-epoxy-3-hydroxy-14β-[(3-phenylpropyl)oxy]-morphinan-6β-ylamino}-acetic acid dihydrochloride.

It has now been found that the compounds of the pertinent invention represent effective opioid receptor ligands of the type 6-aminomorphinan and exhibit a high therapeutic application potential as analgesics, as immunomodulators with immunostimulating or immunosuppressive effect, as cancer therapeutics, inflammation inhibitors, as anti-rheumatics, diuretics, anorectics, as an agent against diarrhoea, anaesthetics or as neuroprotective active substances.

The compounds quoted in the claims are therefore potentially applicable to the treatment of pain, functional intestinal diseases, such as abdominal pain, intestinal obstruction (ileus) or obstipation, for the treatment of mammals, in particular humans, for the treatment of Raynaud's disease, for the treatment of complaints caused by vasoconstriction, for the treatment of dysmenorrhoea, angina pectoris, myocardial infarct, emphysema, bronchial spasms, chronic obstructive bronchitis, rheumatic complaints, nephrosis, nephritis in conjunction with rheumatic diseases, for the treatment of tumours, phaeochromocytoma, Addison's disease, hepatic cirrhosis, chronic inflammation of the small and large intestines (e.g. irritable colon syndrome—colon irritabile, colitis ulcerosa, morbus Crohn), addiction withdrawal of, for example, opiates, cocaine or alcohol, or for the treatment of psychic diseases such as dysphoria or schizophrenia.

The compounds of this invention are suitable for application in the production of a medicament for the treatment of pain, including acute and chronic pain, on the locomotor system such as pain in the neck, back, hip, knee, shoulder or myofacial pain, treatment of complex regional pain syndromes, phantom pain, facial neuralgia, rheumatalgia, cancer pain, pain from burns, pain after accidents, pain due to chronic inflammation, visceralgia, headaches such as for example tension headaches, cervically related headache or migraine, pain after central lesions such as for example with paraplegia or thalamic lesions, neuralgic pain such as zoster neuralgia, postzoster neuralgia, ischaemic pain such as angina pectoris or peripheral occlusive arterial disease, postoperative pain, neuropathic pain such as pain with diabetic neuropathy, pain after virus infections or pain after nerve lesions.

The pharmaceutical compositions according to the invention, which contain a compound of this invention and/or a pharmaceutically acceptable salt of it as active ingredient together with a pharmaceutically acceptable carrier substance, are suitable for the treatment of the conditions quoted in the description.

The application according to the invention includes application as analgesic, immunomodulating, antitumour, antiproliferative, anti-inflammatory, antirheumatic, diuretic, anorectic, antidiarrhoeal, anaesthetic, neuroprotective active substance and as active substance for the prevention and treatment of intestinal obstruction (ileus).

Preferred applications take place for the production of a medicament for the treatment of pain, functional intestinal diseases, of the Raynaud's disease, for the treatment of complaints caused by vasoconstriction, angina pectoris, myocardial infarct, emphysema, bronchial spasms, chronic obstructive bronchitis, rheumatic complaints (including rheumatoid arthritis, arthrosis, osteoarthritis, spondylosis, lumbago, lupus erythematosus, spondyarthropathy), nephrosis, nephritis in conjunction with rheumatic diseases, for the treatment of tumours, cancer, phaeochromocytoma, Addison's disease, hepatic cirrhosis, chronic inflammation of the small and large intestines (e.g. irritable colon syndrome—colon irritabile, colitis ulcerosa, morbus Crohn), for the treatment of drug abuse, psychic diseases, erectile dysfunction and/or for the suppression of rejection of transplants after transplantation on mammals, particularly on humans.

Surprisingly it was also found that the compounds of this invention were not capable of overcoming the blood-brain barrier or only to a slight extent, and therefore a special significance could be attributed to them with regard to their application as peripherally effective therapeutics, for example as medicaments for the treatment of pain, rheumatic therapy, suppression of organ rejection after transplantations on mammals, particularly humans and also for the treatment of erectile disturbances. The limited access to the central nervous system is accompanied by a much reduced rate of side effects relating to central side effects such for example nausea, vomiting, sedation, dizziness, confusion, respiratory depression and mania.

In addition, it was surprisingly found that the compounds of this invention have a very long analgesically effective period. This enables a lower dosage and less frequent administration of the medicament, which results in a lower rate of side effects and toxicity as well as a higher readiness of patients to take the medicament.

DETAILED DESCRIPTION OF THE PRESENTLY PREFERRED EMBODIMENTS

Production of the Compounds

The compounds according to this invention, which are represented by the formula (I), can be obtained with the aid of the following methods:

Starting from thebaine of the formula (II),

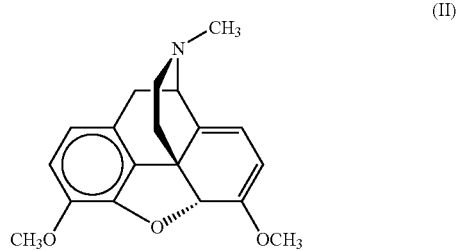

this compound is reacted with dialkylsulphates, fluorosulphonic acid alkylesters, alkylsulphonic acid alkylesters, arylsulphonic acid alkylesters, alkylhalogenides, aralkyihalogenides, alkylsulphonic acid aralkylesters, arylsulphonic acid aralkylesters, arylalkenylhalogenides, chloroformic acid esters or similar in solvents such as tetrahydrofuran, 1,2-dimethoxyethane, diethylether or similar in the presence of a strong base such as n-butyllithium, lithium diethylamide, lithium diisopropylamide or similar at low temperatures (−20° C. to −80° C.) (see Boden et al., J. Org. Chem., Vol 47, pp. 1347-1349, 1982; Schmidhammer et al., Helv. Chim. Acta, Vol. 71, pp. 642-647, 1988; Gates et al., J. Org. Chem., Vol. 54, pp. 972-975, 1984) to obtain the compounds of formula (III), where $R_3$ is $C_1$-$C_6$-alkyl; $C_2$-$C_6$-alkenyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; alkoxyalkyl, where alkoxy is $C_1$-$C_6$-alkoxy and alkyl is $C_1$-$C_6$-alkyl; $CO_2(C_1$-$C_6$-alkyl); $CO_2H$.

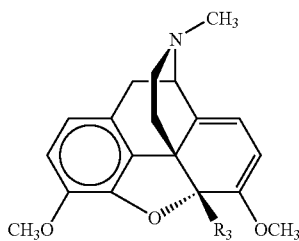

(III)

The compounds of formula (III) or thebaine (formula (II)) can be converted into the corresponding 14-hydroxycodeinones of formula (IV),

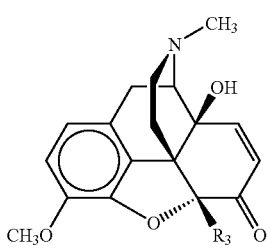

(IV)

where $R_3$ represents hydrogen; $C_1$-$C_6$-alkyl; $C_2$-$C_6$-alkenyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; alkoxyalkyl, where alkoxy is $C_1$-$C_6$-alkoxy and alkyl is $C_1$-$C_6$-alkyl; $CO_2(C_1$-$C_6$-alkyl). This reaction is carried out with performic acid (see H. Schmidhammer et al., Helv. Chim. Acta, Vol. 71, 1801-1804, 1988), m-chloroperbenzoic acid or similar at temperatures between 0° C. and 60° C. The preferred method is the reaction with performic acid at 0° C. to 40° C.

These 14-hydroxycodeinones of formula (IV) are subsequently reacted with dialkylsulphates, alkylhalogenides, alkenylhalogenides, alkinylhalogenides, arylalkylhalogenides, arylalkenylhalogenides, arylalkinylhalogenides or chloroformiates in solvents such as N,N-dimethylformamide (DMF) or tetrahydrofuran (THF) in the presence of a strong base such as sodium hydride, potassium hydride or sodium amide in order to obtain the compounds of formula (V),

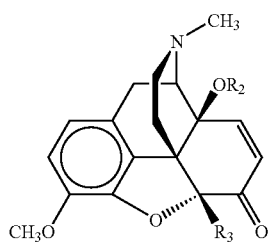

(V)

where $R_3$ is defined as above; and $R_2$ represents hydrogen; $C_1$-$C_6$-alkyl; $C_2$-$C_6$-alkenyl; $C_2$-$C_6$-alkinyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl; $C_1$-$C_6$-alkanoyl; $C_3$-$C_6$-alkenoyl; $C_3$-$C_6$-alkinoyl; $C_7$-$C_{16}$-arylalkanoyl, where aryl is $C_6$-$C_{10}$-aryl and alkanoyl is $C_1$-$C_6$-alkanoyl; $C_9$-$C_{16}$-arylalkenoyl, where aryl is $C_6$-$C_{10}$-aryl and alkenoyl is $C_3$-$C_6$-alkenoyl; $C_9$-$C_{16}$-arylalkinoyl, where aryl is $C_6$-$C_{10}$-aryl and alkinoyl is $C_3$-$C_6$-alkinoyl.

These compounds are then reduced to compounds of formula (VI) using catalytic hydrogenation via a catalyst such as Pd/C, PdO, Pd/$Al_2O_3$, Pt/C, $PtO_2$, Pt/$Al_2O_3$ or similar in solvents such as alcohols, alcohol/water mixtures, glacial acetic acid or similar,

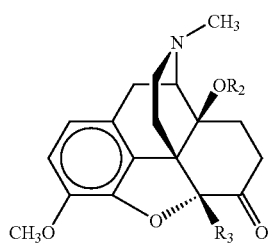

(VI)

where $R_2$ and $R_3$ are defined as above.

The following N-demethylation is carried out with chloroformiates or bromocyanogens in solvents such as 1,2-dichloromethane, chloroform or similar and compounds of the formula (VII) are obtained,

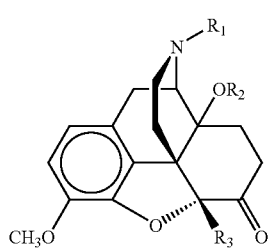

(VII)

where $R_1$ represents $CO_2CH(Cl)CH_3$, $CO_2CH=CH_2$, $CO_2CH_2CCl_3$, $CO_2CH_2CH_3$, $CO_2Ph$, $CN$ or similar; and $R_2$ and $R_3$ are defined as above.

The carbamates of formula (VII) are split either by reflux heating in alcohols (in the case of 1-chloroethylcarbamates) or by the addition of hydrogen halogenides or halogens followed by reflux heating in alcohols (in the case of vinylcarbamates) and the cyanamides of formula (VII) are obtained by acid or alkali hydrolysis, whereby N-Nor compounds of formula (VIII) are obtained,

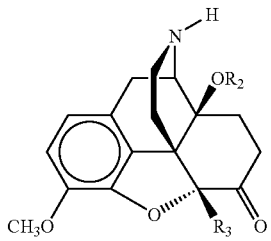

(VIII)

in which $R_2$ and $R_3$ are defined as above.

The N-alkylation of the compounds of formula (VIII) is achieved with alkylhalogenides, dialkylsulphates, alkenylhalogenides, alkinylhalogenides, cycloalkylalkylhalogenides, cycloalkenylalkylhalogenides, arylalkylhalogenides, arylalkenylhalogenides, arylalkinylhalogenides or similar in solvents such as dichloromethane, chloroform or N,N-dimethylformamide in the presence of a base such as sodium bicarbonate, potassium carbonate, triethylamine or similar and therefore compounds of the formula (IX) are obtained,

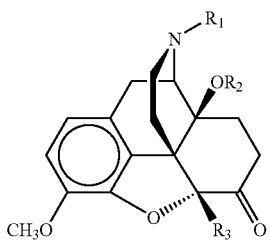

(IX)

where $R_2$ and $R_3$ are defined as above; and $R_1$ represents hydrogen; $C_1$-$C_6$-alkyl; $C_2$-$C_6$-alkenyl; $C_2$-$C_6$-alkinyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl.

Ether splitting of these compounds of the formula (IX) with boron tribromide (in a solvent with dichloromethane or chloroform) at 0° C., 48% hydrobromic acid (reflux heating), with sodium alkanthiolates (in a solvent such as N,N-dimethylformamide) or with other generally well-known ether splitting reagents, gives phenolic compounds of the formula (X),

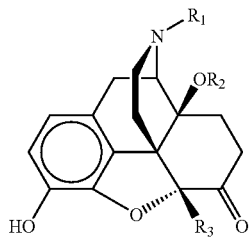

(X)

in which $R_1$, $R_2$ and $R_3$ are defined as above.

The 3-O alkylation of the compounds of formula (X) are achieved with alkylhalogenides, dialkylsulphates, alkenylhalogenides, alkinylhalogenides, cycloalkylalkylhalogenides, cycloalkylalkenylhalogenides, arylalkylhalogenides, arylalkenylhalogenides, arylalkinylhalogenides or similar in solvents such as dichloromethane, chloroform, acetone or N,N-dimethylformamide in the presence of a base such as sodium bicarbonate, potassium carbonate, triethylamine or similar; 3-O acylation of the compounds of the formula (X) is achieved with carboxylic acid halogenides, carboxylic acid anhydrides or similar in solvents such as dichloromethane, chloroform, acetone or N,N-dimethylformamide, pyridine or similar and therefore compounds of the formula (XI) are obtained,

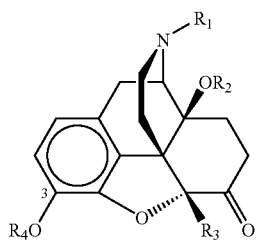

(XI)

where $R_1$, $R_2$ and $R_3$ are defined as above; $R_4$ represents $C_1$-$C_6$-alkyl; $C_2$-$C_6$-alkenyl; $C_2$-$C_6$-alkinyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl; $C_1$-$C_6$-alkanoyl; $C_3$-$C_6$-alkenoyl; $C_3$-$C_6$-alkinoyl; $C_7$-$C_{16}$-arylalkanoyl, where aryl is $C_6$-$C_{10}$-aryl and alkanoyl is $C_1$-$C_6$-alkyl; $C_9$-$C_{16}$-arylalkenoyl, where aryl is $C_6$-$C_{10}$-aryl and alkenoyl is $C_3$-$C_6$-alkenoyl; $C_9$-$C_{16}$-arylalkinoyl, where aryl is $C_6$-$C_{10}$-aryl and alkinoyl is $C_3$-$C_6$-alkinoyl.

The compounds of the formula (XI) are reacted with ammonium acetate, primary and secondary amines, hydroxyamine hydrochloride, amino acids, amino acid esters or similar in solvents such as alcohols, N,N-dimethylformamide or toluol and imines of the formula (XII) and iminium salts of the formula (XIII) are obtained,

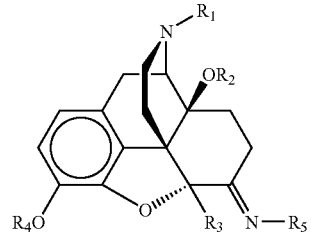

(XII)

-continued

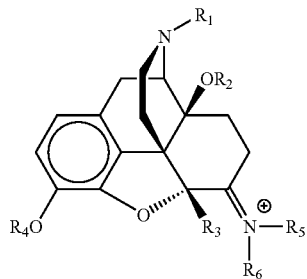

(XIII)

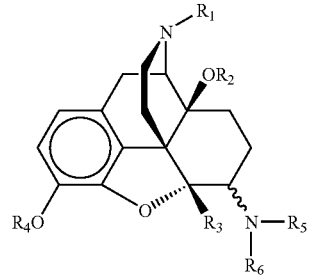

(XIV)

in which $R_1$, $R_2$, $R_3$ and $R_4$ are defined as above; and $R_5$ and $R_6$, which may be the same or different, represent hydrogen, hydroxyl; $C_1$-$C_6$-alkyl; $C_2$-$C_6$-alkenyl; $C_2$-$C_6$-alkinyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl; CH(A)$CO_2$B, where A is hydrogen; hydroxyl; $C_1$-$C_6$-alkyl; $C_2$-$C_6$-alkenyl; $C_2$-$C_6$-alkinyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl; amino; $C_1$-$C_6$-alkylamino; guanidino; $C_1$-$C_6$-alkylguanidino; $C_1$-$C_6$-alkyl-$CO_2$B; and B represents hydrogen; $C_1$-$C_6$-alkyl; $C_2$-$C_6$-alkenyl; $C_2$-$C_6$-alkinyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl.

The reduction of the imines and iminium salts occurs with complex metal hydrides such as lithium aluminium hydride, lithium boron hydride, sodium boron hydride and sodium cyanoboron hydride or similar in alcohols, with borane tetrahydrofuran or similar in tetrahydrofuran (THF), with cyclohexene or cyclohexadien or similar in the presence of a hydrogenating catalyst such as Pd/C, with hydrogen in the presence of a hydrogenation catalyst such as Pd/C, PdO, Pd/$Al_2O_3$, Pt/C, Pt/C (sulphidised), $PtO_2$, Pt/$Al_2O_3$, Rh/C, Rh/$Al_2O_3$ or similar in solvents such as alcohols, glacial acetic acid or similar and the corresponding amines of formula (XIV) are obtained, in which $R_1$, $R_2$, $R_3$ and $R_4$ are defined as above; and $R_5$ and $R_6$, which may be the same or different, represent hydrogen; $C_1$-$C_6$-alkyl; $C_2$-$C_6$-alkenyl; $C_2$-$C_6$-alkinyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl; CH(A)$CO_2$B, where A is hydrogen; hydroxyl; $C_1$-$C_6$-alkyl; $C_2$-$C_6$-alkenyl; $C_2$-$C_6$-alkinyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl; amino; $C_1$-$C_6$-alkylamino; guanidino; $C_1$-$C_6$-alkylguanidino; $C_1$-$C_6$-alkyl-$CO_2$B; and B represents hydrogen; $C_1$-$C_6$-alkyl; $C_2$-$C_6$-alkenyl; $C_2$-$C_6$-alkinyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl. These compounds correspond to the compounds of formula (I) according to the invention,

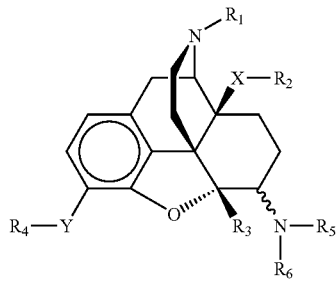

(I)

where $R_1$, $R_2$, $R_3$, $R_4$, $R_5$ and $R_6$ are defined as above and X and Y are oxygen.

If $R_5$ and $R_6$ in the compounds of formula (I) according to the invention are hydrogen and X and Y oxygen, these 6-amino compounds of formula (XV),

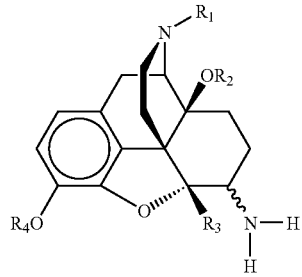
(XV)

in which $R_1$, $R_2$, $R_3$ and $R_4$ are defined as above, can be reacted with guanidination agents such as N,N'-bis-(tert.-butoxycarbonyl)-S-methylisothiourea in the presence of salts such as mercury(II) chloride, silver nitrate or similar as well as bases such as triethylamine, N-ethyldiisopropylamine or similar in solvents such as N,N-dimethylformamide or similar and, depending on the amount of guanidination agent used, either compounds of formula (XVI) or compounds of formula (XVIa) are obtained,

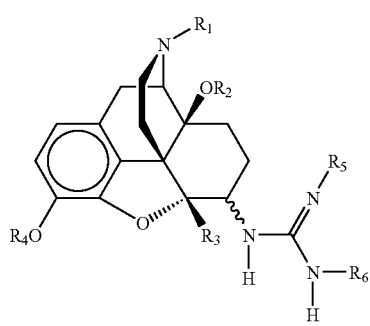
(XVI)

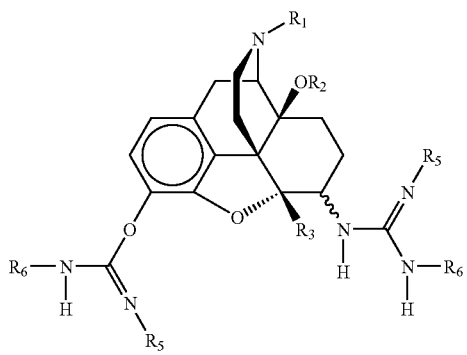
(XVIa)

in which $R_1$, $R_2$, $R_3$ and $R_4$ are defined as above; and $R_5$ and $R_6$, which may be the same or different, represent hydrogen; a protective group such as for example tert.-butoxycarbonyl (Boc) or benzyloxycarbonyl (Z); $C_2$-$C_7$-alkyloxycarbonyl; $C_3$-$C_8$-alkenyloxycarbonyl; $C_3$-$C_8$-alkinyloxycarbonyl; $C_8$-$C_{17}$-arylalkyloxycarbonyl, where aryl is $C_6$-$C_{10}$-aryl and alkyloxy is $C_1$-$C_6$-alkyloxy; $C_9$-$C_{17}$-arylalkenyloxycarbonyl, where aryl is $C_6$-$C_{10}$-aryl and alkenyloxy is $C_2$-$C_6$-alkenyloxy; $C_9$-$C_{17}$-arylalkinyloxycarbonyl, where aryl is $C_6$-$C_{10}$-aryl and alkinyloxy is $C_2$-$C_6$-alkinyloxy; $C_2$-$C_7$-alkanoyl; $C_8$-$C_{17}$-aralkanoyl, where aryl is $C_6$-$C_{10}$-aryl and alkyl is $C_2$-$C_7$-alkyl; $C_1$-$C_6$-alkyl; $C_2$-$C_6$-alkenyl; $C_2$-$C_6$-alkinyl; $C_4$-$C_{16}$-cycloalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl.

The following splitting of the protective groups ($R_5$, $R_6$) with acids such as hydrohalic acids, trifluoroacetic acid, tetrafluoroboric acid or similar in solvents such as dichloromethane, diethylether, alcohols, alcohol/water mixtures or similar produces the 6-guanidinyl compounds of formula (XVII),

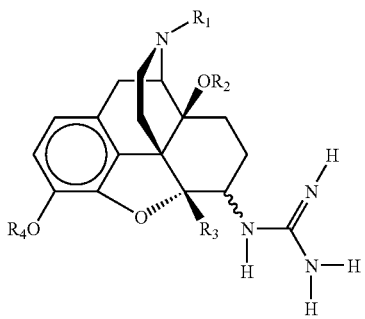
(XVII)

in which $R_1$, $R_2$, $R_3$ and $R_4$ are defined as above. These compounds correspond to the compounds of formula (I) according to the invention, in which $R_1$, $R_2$, $R_3$ and $R_4$ are defined as above and $R_5$ is formamidinyl, $R_6$ hydrogen, X and Y oxygen.

If $R_5$ and $R_6$ are hydrogen in the compounds of formula (I) according to the invention and X and Y are oxygen, these 6-amino compounds of formula (XV),

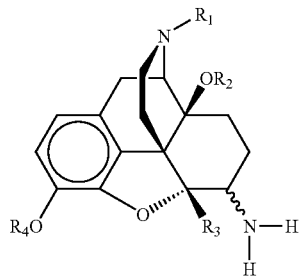
(XV)

in which $R_1$, $R_2$, $R_3$ and $R_4$ are defined as above, e.g. with N-acyl-2-(methylmercapto)-2-imidazoline (which can be easily represented by commercially available 2-(methylmercapto)-2-imidazoline hydro-iodide; see Mundla et al., Tetrahedron Lett., Vol. 41, p. 6563, 2000) or similar can be reacted in solvents such as acetic acid, acetic acid/ethanol 1:10; acetic acid/isopropanol 1:10 or similar and the compounds of formula (XVIII) obtained,

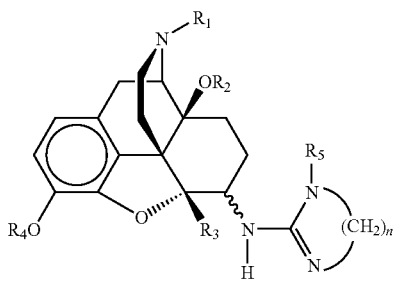

(XVIII)

in which $R_1$, $R_2$, $R_3$ and $R_4$ are defined as above; and $R_5$ is hydrogen; a protective group such as for example tert.-butoxycarbonyl (Boc) or benzyloxycarbonyl (Z); $C_2$-$C_7$-alkyloxycarbonyl; $C_3$-$C_8$-alkenyloxycarbonyl; $C_3$-$C_8$-alkinyloxycarbonyl; $C_8$-$C_{17}$-arylalkyloxycarbonyl, where aryl is $C_6$-$C_{10}$-aryl and alkyloxy is $C_1$-$C_6$-alkyloxy; $C_9$-$C_{17}$-arylalkenyloxycarbonyl, where aryl is $C_6$-$C_{10}$-aryl and alkenyloxy is $C_2$-$C_6$-alkenyloxy; $C_9$-$C_{17}$-arylalkinyloxycarbonyl, where aryl is $C_6$-$C_{10}$-aryl and alkinyloxy is $C_2$-$C_6$-alkinyloxy; $C_2$-$C_7$-alkanoyl; $C_8$-$C_{17}$-aralkanoyl, where aryl is $C_6$-$C_{10}$-aryl and alkyl is $C_2$-$C_7$-alkyl; $C_1$-$C_6$-alkyl; $C_2$-$C_6$-alkenyl; $C_2$-$C_6$-alkinyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, whereby aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl; n is a number between 2 and 4.

The following splitting of the protective group ($R_5$) takes place by reflux heating of the compounds of formula (XVIII) in solvents such as acetic acid/ethanol 1:10, acetic acid/isopropanol 1:10, methanol /water 3:1 or similar and the compounds of formula (XIX) are obtained,

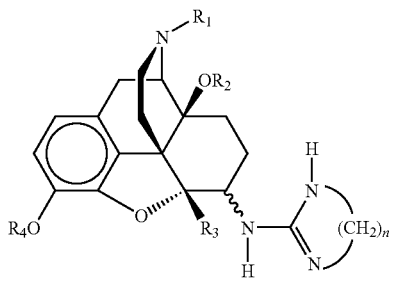

(XIX)

in which $R_1$, $R_2$, $R_3$ and $R_4$ are defined as above; n is a number between 2 and 4. These compounds correspond to the compounds of the formula (I) according to the invention, in which $R_1$, $R_2$, $R_3$ and $R_4$ are defined as above, $R_5$ is either 4,5-dihydro-1H-imidazol-2-yl (n=2), 1,4,5,6-tetrahydropyrimidine-2-yl (n=3) or 4,5,6,7-tetrahydro-1H-[1,3]diazepine-2-yl (n=4), $R_6$ is hydrogen and X and Y are oxygen.

An alternative path starts with compounds of formula (XX), in which $R_1$ and $R_3$ are defined as above (see, for example, formula IX) (see Weiss et al., J. Amer. Chem. Soc., Vol. 77, p. 5891, 1955; Iijima et al., J. Med. Chem., Vol. 21, pp. 398-400, 1978; Coop et al., J. Org. Chem., Vol. 63, pp. 4392-4396, 1998; Schmidhammer et al., Helv. Chim. Acta, Vol. 71, pp. 1801-1804, 1988; Schmidhammer et al., Helv. Chim. Acta, Vol. 73, pp. 1986-1990, 1990).

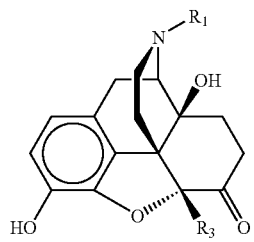

(XX)

The ketones of formula (XX) are reacted in the presence of an acid such as methane sulphonic acid or similar with ethylene glycol (as reagent and solvent) to form the compounds of formula (XXI),

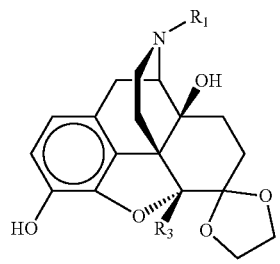

(XXI)

in which $R_1$ and $R_3$ are defined as above.

The introduction of a 3-O protective group in compounds of formula (XXI) is achieved, for example, with benzyl halogenides or trialkyl halogen silanes in solvents such as dichloromethane, chloroform, acetone or N,N-dimethylformamide or similar in the presence of a base such as sodium bicarbonate, potassium carbonate, triethylamine or similar and therefore compounds of the formula (XXII) are obtained,

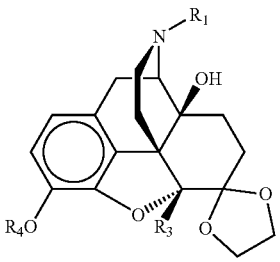

(XXII)

where $R_1$ and $R_3$ are defined as above; $R_4$ is a protective group such as benzyl, tri-($C_1$-$C_6$-alkyl)silyl or tris-($C_7$-$C_{16}$-arylalkyl)silyl, where aryl is $C_6$-$C_{10}$-aryl and alkyl is $C_1$-$C_6$-alkyl.

These 14-hydroxy compounds are following reacted with dialkylsulphates, alkylhalogenides, alkenylhalogenides, alkinylhalogenides, arylalkylhalogenides, arylalkenylhalogenides, arylalkinylhalogenides or chloroformiates in solvents such as N,N-dimethylformamide (DMF) or tetrahydrofuran (THF) in the presence of a strong base such as sodium hydride, potassium hydride or sodium amide to obtain the compounds of formula (XXIII),

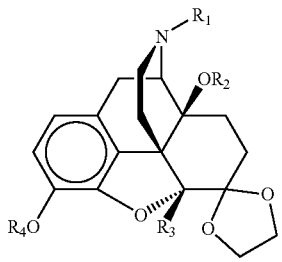

where $R_1$, $R_2$ and $R_3$ are defined as above (see, for example, formula (IX)), $R_4$ is defined as in formula (XXII). If $R_2$ and $R_4$ are benzyl, compounds of the formula (XXI) can be directly reacted with two equivalents of benzyl bromide in DMF in the presence of sodium hydride, forming 3,14-O-dibenzyl derivatives of the formula (XXIII), in which $R_2$ and $R_4$ are benzyl and $R_1$ and $R_3$ are defined as above.

The acidic splitting of the 3-O protective group and the ketal function of the compounds with the formula (XXIII) is carried out in one step with an acid such as hydrochloric acid in methanol, tetrafluoroboric acid in dichloromethane, trifluoroacetic acid and compounds of the formula (X) are obtained (see 1st route),

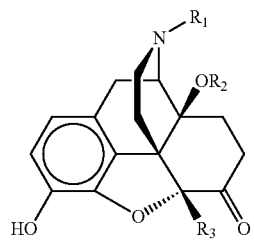

(X)

in which $R_1$, $R_2$ and $R_3$ are defined as above.

Alternatively to this, if $R_4$ in the compounds of formula (XXIII) is benzyl, one can, through hydrogenolysis of the 3-O-benzyl binding with hydrogen gas in the presence of a catalyst such as Pd/C, PdO, Pd/$Al_2O_3$, Pt/C, $PtO_2$, Pt/$Al_2O_3$ or similar in solvents such as alcohols, alcohol/water mixtures, glacial acetic acid or similar, followed by acid hydrolysis of the ketal function in position 6 with, for example, methanol and concentrated hydrochloric acid obtain compounds of the formula (X).

The compounds of the formula (X) are reacted corresponding the first scheme via the compounds of the formulae (XI) to (XIV) to the compounds of formula (I) according to the invention.

The following examples describe the manufacture of the compounds according to the invention in detail.

EXAMPLE 1

Synthesis of (4,5α-epoxy-3-hydroxy-14β-methoxy-17-methylmorphinan-6α-ylamino)-acetic acid-tert.-butylester (Compound 1) and (4,5α-epoxy-3-hydroxy-14β-methoxy-17-methylmorphinan-6β-ylamino)-acetic acid-tert.-butylester (Compound 2)

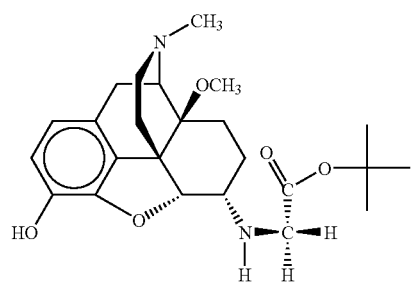

Verbindung 1

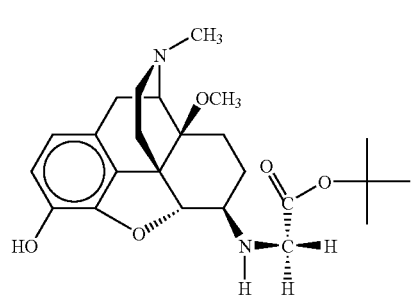

Verbindung 2

A solution of 14-O-methyloxymorphone hydrobromide (H. Schmidhammer et al., Helv. Chim. Acta 1990, Vol. 71, pp. 1179-1783) (2.36 g, 5.96 mmol) and glycine-tert.-butylester hydrochloride (1.11 g, 6.62 mmol) in absolute MeOH (100 ml) was stirred for 1 hour under $N_2$ at room temperature. Then a solution of NaCNBH$_3$ (0.55 g, 8.75 mmol) in MeOH (50 ml) was added in drops over 20 min. and the solution stirred further under $N_2$ at room temperature. After 19 h $H_2O$ (20 ml) was added and the mixture evaporated. The residue was mixed with $H_2O$ (400 ml), alkalized with concentrated ammonia, saturated with NaCl and extracted with $Et_2O$ (1×100 ml, 3×50 ml). The combined organic phases were washed with $H_2O$ (1×200 ml) and saturated NaCl solution (1×200 ml), dried ($Na_2SO_4$) and evaporated. The aqueous phase was extracted with $CH_2Cl_2$/i-PrOH 4:1 (1×100 ml, 3×50 ml). The combined organic phases were treated in the same way as the ether phase described above. From the 1st extraction ($Et_2O$) 1.05 g of a yellow oil were obtained, containing the two products (Compound 1 and Compound 2). From the second extraction (CH₂Cl₂/i-PrOH) 0.72 g of a yellow oil were obtained, containing, apart from the two products, also the corresponding 6-hydroxy derivatives. The two products were separated and purified by MPLC (p=5 bar, silica gel 60, CH₂Cl₂/MeOH 10:1).

Compound 1: Yield: 0.28 g (11%) of orange foam resin. IR (KBr): 3407 (OH), 1731 (C=O) cm⁻¹; ¹H-NMR (CDCl₃): δ 6.66 (d, J=8.1, 1 arom. H); 6.48 (d, J=8.1, 1 arom. H); 5.05 (s, br, OH—C(3), —NH—C(6)); 4.65 (d, J=3.6, H—C(5)); 3.42 (s, C(6)-NH—C$\underline{H}_2$—); 3.21 (s, CH₃O—C(14)); 2.36(s, CH₃N); 1.43(s, —COOC(C$\underline{H}_3$)₃); Cl-MS: m/z 431 (M⁺+1).

Compound 2: Yield: 0.63 g (24%) of yellow foam resin. IR (KBr): 3421 (OH), 1729 (C=O) cm⁻¹; ¹H-NMR (CDCl₃): δ 6.68 (d, J=8.0, 1 arom. H); 6.53 (d, J=8.0, 1 arom. H); 4.71 (s, br, OH—C(3), C(6)-NH—); 4.47 (d, J=7.0, H—C(5)); 3.48 (d, J=17.3, 1 H, C(6)-NH—C$\underline{H}_2$—); 3.32 (d, J=17.3, 1 H, C(6)-NH—C$\underline{H}_2$—); 3.19 (s, CH₃O—C(14)); 2.42 (s, CH₃N); 1.42 (s, —COOC(C$\underline{H}_3$)₃); Cl-MS: m/z 431 (M⁺+1).

EXAMPLE 2

Synthesis of (4,5α-epoxy-3-hydroxy-14β-methoxy-17-methylmorphinan-6α-ylamino)-acetic acid sesqui (trifluoroacetate) (Compound 3.1,5 TFA)

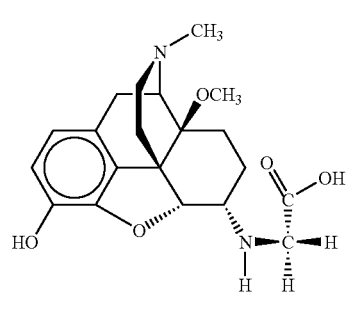

Verbindung 3

A mixture of Compound 1 (0.18 g, 0.42 mmol) and 30% trifluoroacetic acid (TFA) in CH₂Cl₂ (7 ml) was stirred at room temperature for 9 h and then evaporated. The residue (0.26 g of orange foam resin) was crystallised out of i-PrOH/Et₂O/MeOH. The expected bis(trifluoroacetate) is not obtained, but instead the sesqui(trifluoroacetate), which has been proven by several elementary analyses. Yield 0.13 g (57%) of beige 3.1,5 TFA: Fp>190° C. (Brkd.); IR (KBr): 3428 (OH), 1677 (C=O) cm⁻¹; ¹H-NMR (D₂O): δ 6.90 (d, J=8.4, 1 arom. H); 6.81 (d, J=8.4, 1 arom. H); 4.47 (dd, ³J=3.0, ⁴J=1.0, H—C(5)); 3.87 (d, J=1.4, C(6)-NH—C$\underline{H}_2$—); 3.35 (s, CH₃O—C(14)); 2.94 (s, CH₃N); ESI-MS: m/z 375 (M⁺+1).

EXAMPLE 3

Synthesis of (4,5α-epoxy-3-hydroxy-14β-methoxy-17-methylmorphinan-6β-ylamino)-acetic acid sesqui (trifluoroacetate) (Compound 4.1,5 TFA)

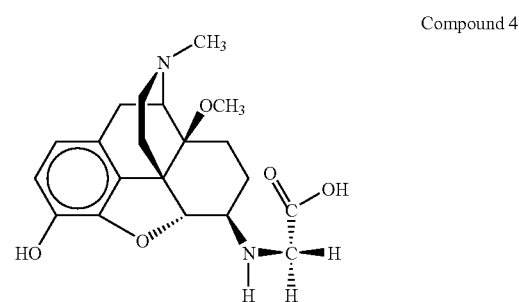

Verbindung 4

A mixture of Compound 2 (0.30 g, 0.70 mmol) and 30% trifluoroacetic acid (TFA) in CH₂Cl₂ (11 ml) was stirred at room temperature for 5 h and then evaporated. The residue (0.43 g of yellow foam resin) was crystallised out of i-PrOH/Et₂O/MeOH. The expected bis(trifluoroacetate) is not obtained, but instead the sesqui(trifluoroacetate), which has been proven by several elementary analyses. Yield 0.21 g (55%) of beige 4.1,5 TFA: Fp>210° C. (Brkd.); IR (KBr): 3419 (OH), 1677 (C=O) cm⁻¹; ¹H-NMR (D₂O); δ 6.89 (d, J=8.6, 1 arom. H); 6.83 (d, J=8.6, 1 arom. H); 4.90 (d, J=7.8, H—C(5)); 4.04 (s, C(6)-NH—C$\underline{H}_2$—); 3.32 (s, CH₃O—C (14)); 2.91 (s, CH₃N); ESI-MS: m/z 375 (M⁺+1).

EXAMPLE 4

Synthesis of (2'S)-2'-(4,5α-epoxy-3-hydroxy-14β-methoxy-17-methylmorphinan-6α-ylamino)-propionic acid-tert.-butylester (Compound 5) and (2'S)-2'-(4,5α-epoxy-3-hydroxy-14β-methoxy-17-methylmorphinan-6β-ylamino)-propionic acid-tert.-butylester (Compound 6)

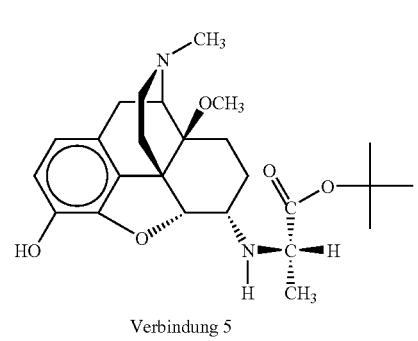

Verbindung 5

-continued

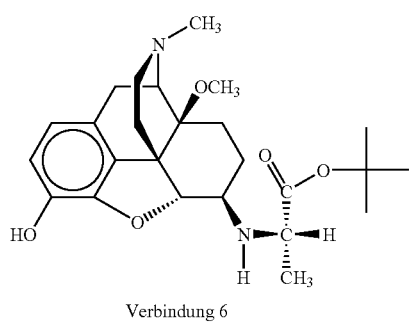

Compound 6

Verbindung 6

A mixture of 14-O-methyloxymorphone hydrobromide (H. Schmidhammer et al. Helv. Chim. Acta 1990, Vol. 71, pp. 1779-1783) (2.54 g, 6.41 mmol), L-alanine-tert.-butylester hydrochloride (1.75 g, 9.63 mmol), absolute EtOH (150 ml), N-ethyldiisopropylamine (2.8 ml, 16.07 mmol) and molecular sieve (2.8 g) was stirred for 5 h under $N_2$ at room temperature. Then a solution of $NaCNBH_3$ (0.51 g, 8.12 mmol) was added drop by drop to EtOH (20 ml) over 20 min. and the solution stirred further under $N_2$ at room temperature. After two days $H_2O$ (5 ml) was added and the mixture evaporated. The residue was mixed with $H_2O$ (200 ml) and extracted with $Et_2O$ (2×100 ml, 2×50 ml). The combined organic phases were washed with saturated NaCl solution (1×200 ml), dried ($Na_2SO_4$) and evaporated. The aqueous phase was extracted with $CH_2Cl_2$ (2×100 ml, 2×50 ml). The combined organic phases were treated in the same way as the ether phase. From the first extraction ($Et_2O$) 1.34 g of a yellow oil were obtained, containing the two products (Compound 5 and Compound 6). From the second extraction ($CH_2Cl_2$) 0.68 g of a yellow oil were obtained, containing, apart from the two products, also the corresponding 6-hydroxy derivatives. The two products were separated and purified by MPLC (p=5 bar, silica gel 60, $CH_2Cl_2$/MeOH 10:1). Compound 5 was crystallised out of methanol and only an analytical amount (50 mg) of Compound 6 could be crystallised out of i-PrOH, the residue (0.75 g) was obtained as a white foam resin.

Compound 5: Yield: 0.32 g (11%) of colourless crystals: Fp 196-200° C.; IR (KBr): 3203 (OH), 1729 (C=O) $cm^{-1}$; $^1$H-NMR ($CDCl_3$): δ 6.69 (d, J=8.2, 1 arom. H); 6.47 (d, J=8.2, 1 arom. H); 4.70 (d, J=3.2, H—C(5)); 3.55 (q, J=6.8, C(6)-NH—C$\underline{H}$($CH_3$)—); 3.19 (s, $CH_3O$—C(14)); 2.35 (s, $CH_3N$); 1.47 (s, —COOC(C$\underline{H}_3$)$_3$); 1.26 (d, J=6.8, C(6)-NH—CH(C$\underline{H}_3$)—); Cl-MS: m/z 445 ($M^+$+1).

Compound 6: Yield: 0.80 g (24%) of colourless crystals and white foam resin: Fp 235-240° C. (Brkd.); IR (KBr): 3423 (OH), 1722 (C=O) $cm^{-1}$; $^1$H-NMR ($CDCl_3$): δ 6.69 (d, J=8.0, 1 arom. H); 6.54 (d, J=8.2, 1 arom. H); 4.39 (d, J=7.2, H—C(5)); 3.32 (q, J=7.0, C(6)-NH—C$\underline{H}$($CH_3$)—); 3.20 (s, $CH_3O$—C(14)); 2.39 (s, $CH_3N$); 1.41 (s, —COOC(C$\underline{H}_3$)$_3$); 1.26 (d, J=6.8, C(6)-NH—CH(C$\underline{H}_3$)—); Cl-MS: m/z 445 ($M^+$+1).

EXAMPLE 5

Synthesis of (2'S)-2'-(4,5α-epoxy-3-hydroxy-14β-methoxy-17-methylmorphinan-6α-ylamino)-propionic acid bis(tetrafluoroborate) (Compound 7.2 HBF$_4$)

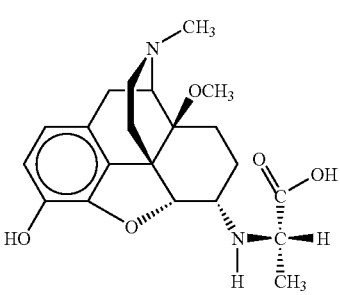

Compound 7

Verbindung 7

A solution of Compound 5 (0.30 g, 0.70 mmol) in $CH_2Cl_2$ (3 ml) was mixed with 54% tetrafluoroboric acid (HBF$_4$) in $Et_2O$ (0.33 ml, 2.39 mmol) and the mixture subjected to ultrasound for 1 h at room temperature. The resulting precipitate was filtered off and dried. Yield 0.21 g (79%) of white 7.2 HBF$_4$: Fp>290° C. (Brkd.); IR (KBr): 3423 (OH), 1741 (C=O), 1064 (B—F) $cm^{-1}$; $^1$H-NMR (D$_2$O): δ 6.90 (d, J=8.0, 1 arom. H); 6.81 (d, J=8.0, 1 arom. H); 5.02 (d, J=2.8, H—C(5)); 4.24 (q, J=7.0, C(6)-NH—C$\underline{H}$($CH_3$)—); 3.35 (s, $CH_3O$—C(14)); 2.94 (s, $CH_3N$); 1.63 (d, J=7.0, C(6)-NH—CH(C$\underline{H}_3$)—).

EXAMPLE 6

Synthesis of (2'S)-2'-(4,5α-epoxy-3-hydroxy-14β-methoxy-17-methylmorphinan-6β-ylamino)-propionic acid bis(tetrafluoroborate) (Compound 8.2 HBF$_4$)

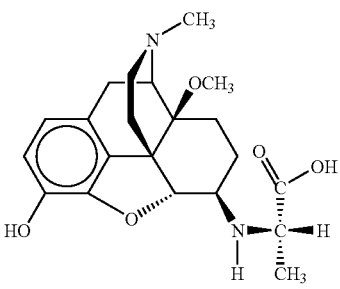

Compound 8

Verbindung 8

A solution of Compound 6 (0.25 g, 0.56 mmol) in $CH_2Cl_2$ (4 ml) was mixed with 54% tetrafluoroboric acid (HBF$_4$) in $Et_2O$ (0.39 ml, 2.85 mmol) and the mixture subjected to ultrasound for 1 h at room temperature. The resulting precipitate was filtered off and dried. Yield 0.28 g (89%) of white 8.2

HBF$_4$: Fp>290° C. (Brkd.); IR (KBr): 3423 (OH), 1720 (C=O),1083 (B—F) cm$^{-1}$; $^1$H-NMR (D$_2$O): δ 6.87 (s, 2 arom. H); 4.86 (d, J=7.6, H—C(5)); 4.31 (q, J=7.0, C(6)-NH—C$_H$(CH$_3$)—); 3.33 (s, CH$_3$O—C(14)); 2.92 (s, CH$_3$N); 1.58 (d, J=7.0, C(6)-NH—CH(CH$_3$)—).

EXAMPLE 7

Synthesis of (2'S)-2'-(4,5α-epoxy-3-hydroxy-14β-methoxy-17-methylmorphinan-6α-ylamino)-3'-phenylpropionic acid-tert.-butylester (Compound 9) and (2'S)-2-(4,5α-epoxy-3-hydroxy-14β-methoxy-17-methylmorphinan-6β-ylamino)-3'-phenylpropionic acid-tert.-butylester (Compound 10)

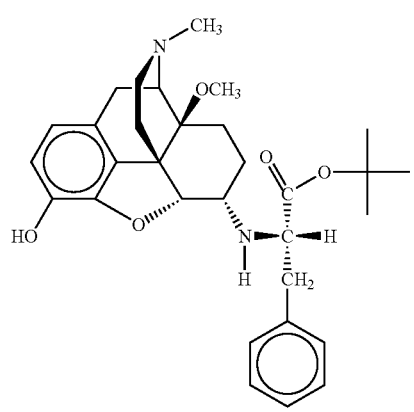

Verbindung 9

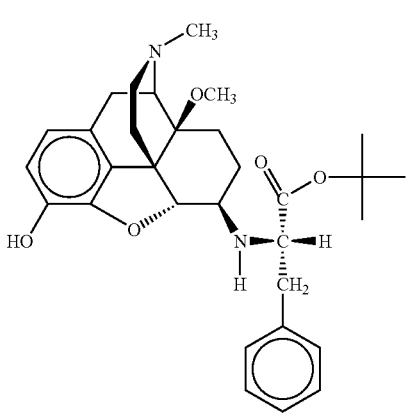

Verbindung 10

A mixture of 14-O-methyloxymorphone hydrobromide (H. Schmidhammer et al., Helv. Chim. Acta 1990, Vol. 71, pp. 1779-1783) (2.70 g, 6.81 mmol), L-phenylalanine-tert.-butylester hydrochloride (2.74 g, 10.63 mmol), absolute EtOH (150 ml), N-ethyldiisopropylamine (3.04 ml, 17.49 mmol) and molecular sieve (3.0 g) was stirred for 2.5 h under N$_2$ at room temperature. Then a solution of NaCNBH$_3$ (0.47 g, 7.48 mmol) added drop by drop to EtOH (20 ml) over 20 min. and the solution stirred further under N$_2$ at room temperature. After three days H$_2$O (10 ml) was added and the mixture evaporated. The residue was mixed with H$_2$O (300 ml) and extracted with CH$_2$Cl$_2$ (1×100 ml, 4×50 ml). The combined organic phases were filtered through Celite, washed with saturated NaCl solution (1×200 ml), dried (Na$_2$SO$_4$) and evaporated. 3.96 g of a yellow oil were obtained from which the two products were each obtained in pure form using MPLC (p=5 bar, silica gel 60, CH$_2$Cl$_2$/MeOH 10:1). 0.68 g of the initial compound (14-O-methyloxymorphone) were retrieved as a brown foam resin.

Compound 9: Yield: 0.34 g (10%) of orange foam resin: IR (KBr): 3336 (OH), 1725 (C=O) cm$^{-1}$; $^1$H-NMR (CDCl$_3$): δ 7.31-7.17 (m, 5 arom. H); 6.71 (d, J=8.0, 1 arom. H); 6.47 (d, J=8.0, 1 arom. H); 4.71 (d, J=3.2, H—C(5)); 3.77-3.69 (m, C(6)-NH—CH(CH$_2$Ph)-); 3.12 (s, CH$_3$O—C(14)); 2.94-2.90(m, C(6)-NH—CH(CH$_2$Ph)-); 2.35 (s, CH$_3$N); 1.32 (s, —COOC(CH$_3$)$_3$); Cl-MS: m/z 521 (M$^+$+1).

Compound 10: Yield: 0.81 g (23%) of orange foam resin: IR (KBr): 3409 (OH), 1724 (C=O) cm$^{-1}$; $^1$H-NMR (CDCl$_3$): δ 7.29-7.17 (m, 5 arom. H); 6.70 (d, J=8.0, 1 arom. H); 6.54 (d, J=8.0, 1 arom. H); 4.39 (d, J=7.4, H—C(5)); 3.51-3.43 (m, C(6)-NH—CH(CH$_2$Ph)-); 3.20 (s, CH$_3$O—C(14)); 2.98-2.78(m, C(6)-NH—CH(CH$_2$Ph)-); 2.44 (s, CH$_3$N); 1.28 (s, —COOC(CH$_3$)$_3$); Cl-MS: m/z 521 (M$^+$+1).

EXAMPLE 8

Synthesis of (2'S)-2'-(4,5α-epoxy-3-hydroxy-14β-methoxy-17-methylmorphinan-6α-ylamino)-3'-phenylpropionic acid bis(tetrafluoroborate) (Compound 11.2 HBF$_4$)

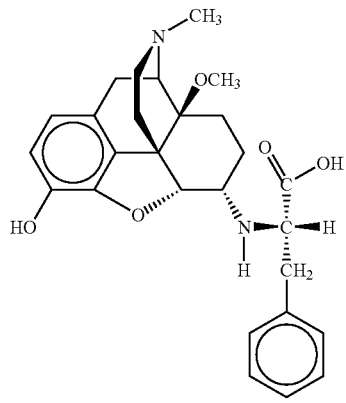

Verbindung 11

A solution of Compound 9 (0.16 g, 0.31 mmol) in CH$_2$Cl$_2$ (3 ml) was mixed with 54% tetrafluoroboric acid (HBF$_4$) in Et$_2$O (0.25 ml, 1.81 mmol) and the mixture subjected to ultrasound for 30 min. at room temperature. Then the mixture was evaporated, the residue (0.21 g orange coloured oil) dissolved in H$_2$O and freeze dried. Yield 0.18 9 (90%) of white lyophilisate: $^1$H-NMR (D$_2$O): δ 7.46-7.35 (m, 5 arom. H); 6.86 (d, J=8.2, 1 arom. H); 6.77 (d, J=8.2, 1 arom. H); 4.90 (d, J=3.4, H—C(5)); 4.46 (t, J=6.8, C(6)-NH—CH(CH$_2$Ph)-); 3.35 (d, J=6.8, C(6)-NH—CH(CH$_2$Ph)-); 3.25 (s, CH$_3$O—C(14)); 2.90 (s, CH$_3$N).

EXAMPLE 9

Synthesis of (2'S)-2'-(4,5α-epoxy-3-hydroxy-14β-methoxy-17-methylmorphinan-6β-ylamino)-3'-phenylpropionic acid bis(tetrafluoroborate) (Compound 12.2 $HBF_4$)

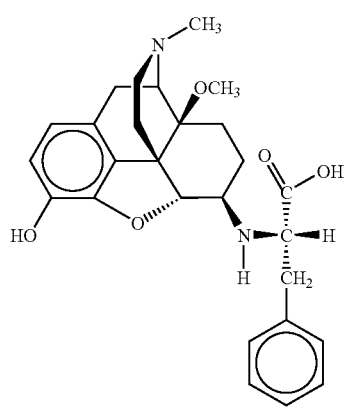

Compound 12

Verbindung 12

A solution of Compound 10 (0.41 g, 0.79 mmol) in $CH_2Cl_2$ (5 ml) was mixed with 54% tetrafluoroboric acid ($HBF_4$) in $Et_2O$ (0.60 ml, 4.35 mmol) and the mixture subjected to ultrasound for 30 min. at room temperature. Then the mixture was evaporated, the residue (0.54 g orange coloured oil) dissolved in $H_2O$ and freeze dried. Yield 0.46 g (90%) of white lyophilisate: $^1$H-NMR ($D_2O$): δ 7.28 (s, 5 arom. H); 6.88 (d, J=8.4, 1 arom. H); 6.81 (d, J=8.4, 1 arom. H); 4.83 (d, J=7.6, H—C(5)); 4.54 (t, J=7.0, C(6)-NH—C$\underline{H}$($CH_2$Ph)-); 3.25 (s, $CH_3O$—C(14)); 2.86 (s, $CH_3N$).

EXAMPLE 10

Synthesis of 6α-amino-4,5α-epoxy-14β-methoxy-17-methylmorphinan-3-ol (Compound 13)

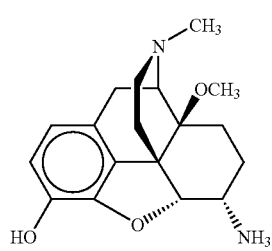

Compound 13

Verbindung 13

A mixture of 14-O-methyloxymorphone hydrobromide (H. Schmidhammer et al., Helv. Chim. Acta 1990, Vol. 71, pp. 1779-1783) (6.22 g, 15.70 mmol), ammonium acetate (12.00 g, 156 mmol), NaCNBH$_3$ (0.81 g, 7.64 mmol) and absolute MeOH (100 ml) were stirred for 23 h under $N_2$ at room temperature. Then the solution acidified (beige precipitate) with concentrated HCl and the mixture evaporated. The residue was dissolved in $H_2O$ (550 ml) and extracted with $CH_2Cl_2$ (1×200 ml) for removal of the components insoluble in water. The aqueous phase was alkalized with conc. ammonia, saturated with NaCl and extracted with $CH_2Cl_2$/i-PrOH 4:1 (2×250 ml, 3×125 ml). The combined organic phases were washed with saturated NaCl solution (1×200 ml), dried ($Na_2SO_4$) and evaporated. The evaporation residue (beige crystals) was recrystallised out of methanol. Yield: 1.95 g (39%) of white powder: Fp>300° C. (Brkd); IR (KBr): 3421 (OH) cm$^{-1}$; $^1$H-NMR ($Me_2$SO-$d_6$): δ 6.55 (d, J=8.0, 1 arom. H); 6.29 (d, J=8.0, 1 arom. H); 4.33 (dd, $^3$J=4.0, $^4$J=0.8, H—C(5)); 3.38 (s, br, OH—C(3), $NH_2$—C(6)); 3.13 (s, $CH_3O$—C(14)); 2.24 (s, $CH_3N$); Cl-MS: m/z 317 ($M^+$+1).

EXAMPLE 11

Synthesis of 6β-dibenzylamino-4,5α-epoxy-14β-methoxy-17-methylmorphinan-3-ol (Compound 14)

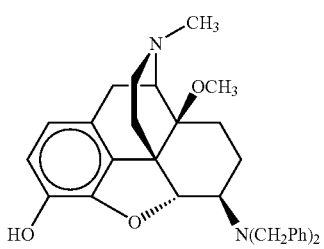

Compound 14

Verbindung 14

A solution of 14-O-methyloxymorphone hydrobromide (H. Schmidhammer et al., Helv. Chim. Acta 1990, Vol. 71, pp. 1779-1783) (2.00 g, 5.05 mmol) in MeOH/$H_2O$ 9:1 (80 ml) was mixed with silver benzoate (1.17 g, 5.11 mmol) and stirred for 90 min. at 40° C. The resulting precipitate of silver bromide was filtered off and the filtrate evaporated. The residue was mixed with EtOH/toluol 2:3 (50 ml) and the solvent drawn off. In this way 2.35 g of 14-O-methyloxymorphone benzoate were obtained as a yellow foam resin. This was mixed with toluol (250 ml), benzoic acid (0.93 g, 7.62 mmol), dibenzylamine (1.49 g, 7.54 mmol) and the tip of a spatula of p-toluol sulphonic acid monohydrate and the mixture was reflux heated for 20 h with the application of a water separator. Then the solution was reduced to a volume of 50 ml, absolute EtOH (220 ml), NaCNBH$_3$ (0.30 g, 4,77 mmol) and a molecular sieve were added and the solution stirred for 6 hours under $N_2$ at room temperature. The mixture was diluted with MeOH (100 ml), filtered and the filtrate evaporated. The residue was mixed with $H_2O$ (550 ml), alkalized with conc. ammonia, and extracted with $CH_2Cl_2$ (1×200 ml, 3×100 ml). The combined organic phases were washed with $H_2O$ (5×300 ml) and saturated NaCl solution (1×200 ml), dried ($Na_2SO_4$) and evaporated. The evaporation residue (2.42 g of brown oil) was crystallised out of methanol. Yield: 1.43 g (57%) of beige crystals: Fp 124-128° C.; IR (KBr): 3178 (OH) cm$^{-1}$; $^1$H-NMR (CDCl$_3$): δ 7.45-7.20 (m, 10 arom. H); 6.56 (d, J=8.1, 1 arom. H); 6.44 (d, J=8.1, 1 arom. H); 4.72 (d, J=6.8, H—C(5)); 3.87 (d, J=14.0, 2 H, (PhC$\underline{H}_2$)$_2$N—C(6)); 3.61 (d, J=14.0, 2 H, (PhC$\underline{H}_2$)$_2$N—C(6)); 3.20 (s, CH$_3$O—C(14)); 2.34 (s, CH$_3$N); Cl-MS: m/z 497 (M$^+$+1).

EXAMPLE 12

Synthesis of 6β-amino-4,5α-epoxy-14β-methoxy-17-methylmorphinan-3-ol (Compound 15)

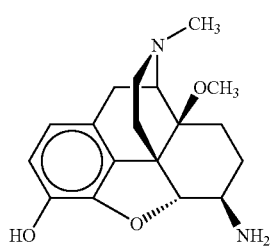

Verbindung 15

A mixture of Compound 14 (1.02 g, 2.05 mmol), 10% Pd/C catalyst (0.52 g), cyclohexene (30 ml) and absolute MeOH (30 ml) were reflux heated for 16 hours under N$_2$. Then the catalyst was filtered off and the filtrate evaporated. The residue (0.66 g of white foam resin) was crystallised out of i-PrOH/Et$_2$O 1:1 (2 ml). Yield: 0.33 g (42%) of beige crystals: Fp>235-239° C.; IR (KBr): 3348 (OH) cm$^{-1}$; $^1$H-NMR (CDCl$_3$): 6.62 (d, J=8.0, 1 arom. H); 6.54 (d, J=8.0, 1 arom. H); 4.26 (d, J=7.0, H—C(5)); 3.22 (s, CH$_3$O—C(14)); 2.36 (s, CH$_3$N); Cl-MS: m/z 317 (M$^+$+1).

EXAMPLE 13

Synthesis of 4,5α-epoxy-6β-[N,N'-bis-(tert.-butoxycarbonyl)guanidinyl]-14β-methoxy-17-methylmorphinan-3-ol (Compound 16)

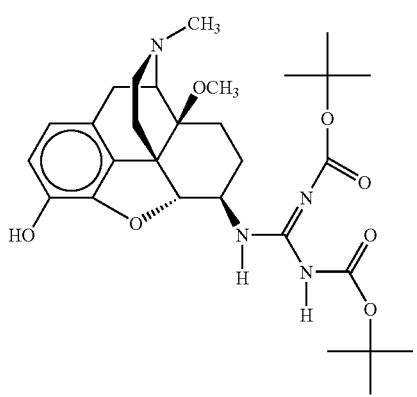

Verbindung 16

A solution of Compound 15 (0.94 g, 2.97 mmol), N,N'-bis-(tert.-butoxycarbonyl)-S-methylisothiourea (0.92 g, 3.17 mmol) and N-ethyldiisopropylamine (0.58 ml, 3.33 mmol) in absolute N,N-dimethylformamide (40 ml) was mixed with silver nitrate (0.54 g, 3.18 mmol) and the mixture stirred for 4 hours. Then the silver mercaptane was filtered off through Celite and washed afterwards with CH$_2$Cl$_2$ (4×50 ml). The filtrate was washed with H$_2$O (10×150 ml) and saturated NaCl solution (2×150 ml), dried (Na$_2$SO$_4$) and evaporated. In this way 1.46 g of a yellow foam resin was obtained which was purified through MPLC (p=5 bar, silica gel 60, CH$_2$Cl$_2$/MeOH/conc. ammonia 95:4, 5:0.5). Yield: 0.77 g (46%) of green foam resin: $^1$H-NMR (CDCl$_3$): δ 11.49 (s, br, NH—COO(CH$_3$)$_3$); 8.59 (d, J=8.0, C(6)-NH—); 6.71 (d, J=8.4, 1 arom. H); 6.56 (d, J=8.4, 1 arom. H); 4.41 (d, J=7.2, H—C(5)); 3.22 (s, CH$_3$O—C(14)); 2.38 (s, CH$_3$N); 1.51 (s, C(C$\underline{H}_3$)$_3$), 1.47 (s, C(C$\underline{H}_3$)$_3$).

EXAMPLE 14

Synthesis of 4,5α-epoxy-6β-guanidinyl-14β-methoxy-17-methylmorphinan-3-ol dihydrochloride (Compound 17.2 HCL)

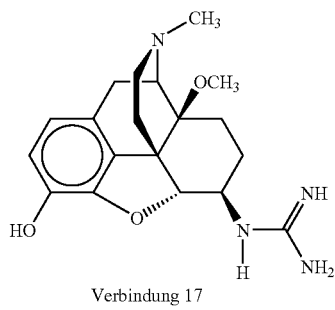

Verbindung 17

A solution of Compound 16 (50 mg, 0.089 mmol) in Et$_2$O (3 ml) was mixed through to a clear acidic reaction with ethereal HCl and with 4 drops of H$_2$O. The mixture was subjected to ultrasound for one hour at room temperature and then evaporated. The residue (40 mg of white foam resin) was dissolved in H$_2$O and freeze dried. Yield: 30 mg (79%) 17.2 HCl as white lyophilisate: $^1$H-NMR (CDCl$_3$): δ 9.59 (s, OH—C(3)); 9.29 (s, br, NH$^+$); 8.53 (d, J=8.0, C(6)-NH—); 7.29 (s, br, C(6)-NH—C(N$\underline{H}_2$)$_2$$^+$), 6.78 (d, J=8.1, 1 arom. H); 6.69 (d, J=8.1, 1 arom. H); 4.49 (d, J=7.2, H—C(5)); 3.26 (s, CH$_3$O—C(14)); 2.84 (s, CH$_3$N).

EXAMPLE 15

Synthesis of 4,5α-epoxy-6α-[N,N'-bis-(tert.-butoxy-carbonyl)guanidinyl]-14β-methoxy-17-methylmorphinan-3-ol (Compound 18)

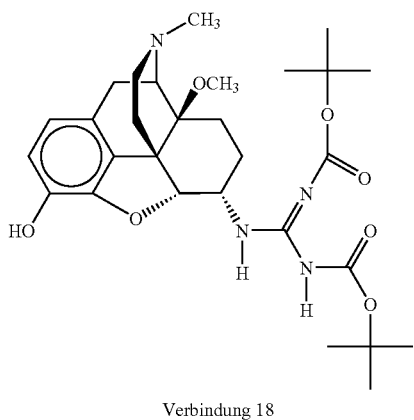

Verbindung 18

A solution of Compound 13 (1.00 g, 3.16 mmol), N,N'-bis-(tert.-butoxycarbonyl)-S-methylisothiourea (1.00 g, 3.44 mmol) and N-ethyldiisopropylamine (0.60 ml, 3.44 mmol) in absolute N,N-dimethylformamide (60 ml) was mixed with silver nitrate (0.55 g, 3.24 mmol) and the mixture stirred for 1.5 h. Then the silver mercaptane was filtered off through Celite and washed afterwards with $CH_2Cl_2$ (4×50 ml). The filtrate was washed with $H_2O$ (6×200 ml) and saturated NaCl solution (1×200 ml), dried ($Na_2SO_4$) and evaporated. In this way 1.85 g of a yellow oil were obtained which was purified through MPLC (p=5 bar, silica gel 60, $CH_2Cl_2$/MeOH 10:1). Yield: 0.67 g (38%) of white foam resin: $^1$H-NMR (CDCl$_3$): δ 11.53 (s, br, NH—COO(CH$_3$)$_3$); 8.81 (d, J=8.0, C(6)-NH—); 6.73 (d, J=8.2,1 arom. H); 6.56 (d, J=8.2, 1 arom. H); 4.66 (dd, $^3$J=2.6, $^4$J=1.6, H—C(5)); 3.25 (s, CH$_3$O—C(14)); 2.35 (s, CH$_3$N); 1.50 (s, 2×C(C$\underline{H}_3$)$_3$).

EXAMPLE 16

Synthesis of 4,5α-epoxy-6α-guanidinyl-14β-methoxy-17-methylmorphinan-3-ol dihydrochloride (Compound 19.2 HCl)

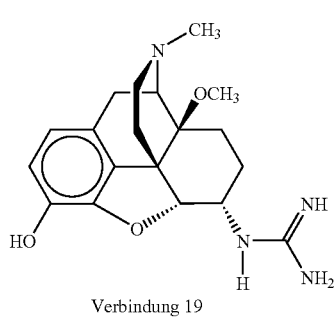

Verbindung 19

A solution of Compound 18 (50 mg, 0.089 mmol) in $Et_2O$ (3 ml) was mixed through to a clear acidic reaction with ethereal HCl and with 4 drops of $H_2O$. The mixture was subjected to ultrasound for 1.5 h at room temperature and then evaporated. The residue (40 mg of white foam resin) was dissolved in $H_2O$ and freeze dried. Yield: 35 mg (92%) 19.2 HCl as white lyophilisate: $^1$H-NMR (CDCl$_3$): δ 9.29 (s, br, NH$^+$); 9.20 (s, OH—C(3)); 7.57 (d, J=8.8, C(6)-NH—); 7.46 (s, br, C(6)-NH—C(N$\underline{H}_2$)$_2^+$), 6.76 (d, J=8.1, 1 arom. H); 6.62 (d, J=8.1, 1 arom. H); 4.70 (d, J=4.0, H—C(5)); 3.36 (s, CH$_3$O—C(14)); 2.88 (s, CH$_3$N).

EXAMPLE 17

Synthesis of 1,3-bis-(tert.-butoxycarbonyl)-2-{4,5α-epoxy-6β-[N,N'-bis-(tert.-butoxycarbonyl )guanidinyl]-14β-methoxy-17-methylmorphinan-3-yl}-isourea (Compound 20)

Verbindung 20

A solution of Compound 15 (0.12 g, 0.38 mmol), N,N'-bis-(tert.-butoxycarbonyl)-S-methylisothiourea (0.24 g, 0.83 mmol) and triethylamine (0.12 ml, 0.86 mmol) in absolute N,N-dimethylformamide (4 ml) was mixed with silver nitrate (0.14 g, 0.82 mmol) and the mixture stirred for 17 h. Then the silver mercaptane was filtered off through Celite and washed afterwards with $CH_2Cl_2$ (4×50 ml). The filtrate was washed with $H_2O$ (5×200 ml) and saturated NaCl solution (1×200 ml), dried ($Na_2SO_4$) and evaporated. In this way 0.10 g of a yellow foam resin was obtained which was purified through MPLC (p=5 bar, silica gel 60, $CH_2Cl_2$/MeOH/conc. ammonia 100:5:0.5). Yield: 45 mg (15%) of white foam resin: $^1$H-NMR ($CDCl_3$): δ 11.54 (s, NH—COO($CH_3$)$_3$); 10.44 (s, br, NH—COO($CH_3$)$_3$); 8.59 (d, J=8.8, C(6)-NH—); 6.91 (d, J=8.0, 1 arom. H); 6.64 (d, J=8.0, 1 arom. H); 4.51 (d, J=4.4, H—C(5)); 3.28 (s, $CH_3$O—C(14)); 2.37 (s, $CH_3$N); 1.51 (s, 2×C(C$\underline{H}_3$)$_3$), 1.47 (s, 2×C(C$\underline{H}_3$)$_3$). FAB-MS: m/z 801 (M$^+$+1).

EXAMPLE 18

Synthesis of 1,3-bis-(tert.-butoxycarbonyl)-2-{4,5α-epoxy-6α-[N,N'bis-(tert.-butoxycarbonyl)guanidinyl]-14β-methoxy-17-methylmorphinan-3-yl}-isourea (Compound 21)

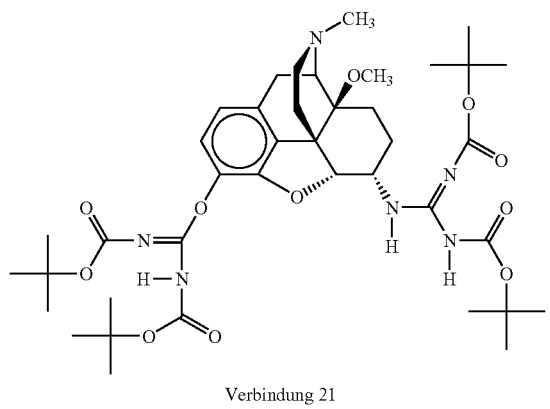

Verbindung 21

A solution of Compound 13 (0.50 g, 1.58 mmol), N,N'-bis-(tert.-butoxycarbonyl)-S-methylisothiourea (1.00 g, 3.54 mmol) and triethylamine (0.5 ml, 4.94 mmol) in absolute N,N-dimethylformamide (15 ml) was mixed with silver nitrate (0.58 g, 3.12 mmol) and the mixture stirred for 20 h. Then the silver mercaptane was filtered off through Celite and washed afterwards with $CH_2Cl_2$ (5×50 ml). The filtrate was washed with $H_2O$ (5×200 ml) and saturated NaCl solution (1×200 ml), dried ($Na_2SO_4$) and evaporated. In this way 1.14 g of a yellow foam resin was obtained which was purified through MPLC (p=5 bar, silica gel 60, $CH_2Cl_2$/MeOH/conc. ammonia 100:5:0.5). Yield: 0.75 g (62%) of white foam resin: $^1$H-NMR ($CDCl_3$): δ 11.56 (s, NH—COO($CH_3$)$_3$); 10.69 (s, br, NH—COO($CH_3$)$_3$); 8.68 (d, J=8.8, C(6)-NH—); 6.87 (d, J=8.0, 1 arom. H); 6.66 (d, J=8.0, 1 arom. H); 4.63 (d, J=3.6, H—C(5)); 3.27 (s, $CH_3$O—C(14)); 2.36 (s, $CH_3$N); 1.51 (s, 4×C(C$\underline{H}_3$)$_3$). ESI-MS: m/z 801 (M$^+$+1).

EXAMPLE 19

Synthesis of (4,5α-epoxy-3-hydroxy-14β-methoxy-17-methylmorphinan-6α-ylamino)-acetic acid-ethylester dihydrochloride (Compound 22.2 HCl) and (4,5α-epoxy-3-hydroxy-14β-methoxy-17-methylmorphinan-6β-ylamino)-acetic acid-ethylester dihydrochloride (Compound 23.2 HCl)

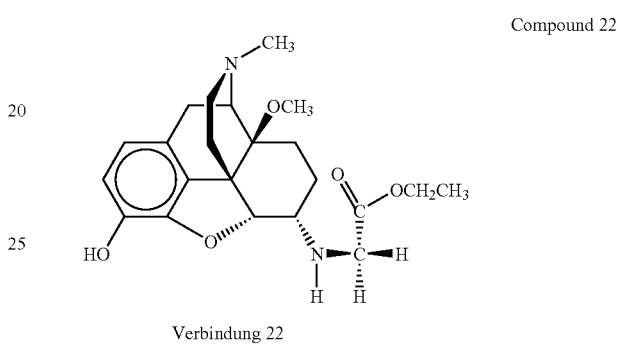

Verbindung 22

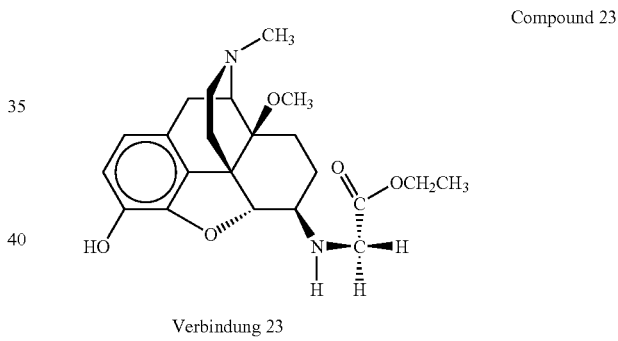

Verbindung 23

A mixture of 14-O-methyloxymorphone hydrobromide (H. Schmidhammer et al., Helv. Chim. Acta 1990, Vol. 71, pp. 1779-1783) (2.00 g, 5.05 mmol), glycine ethylester hydrochloride (1.06 g, 7.59 mmol), absolute EtOH (100 ml), triethylamine (1.8 ml, 12.91 mmol) and molecular sieve (2.5 g) was stirred for 3.5 h under $N_2$ at room temperature. Then $NaCNBH_3$ (0.49 g, 7.80 mmol) was added in a number of portions and the solution stirred further under $N_2$ at room temperature. After 4 days $H_2O$ (5 ml) was added and the mixture evaporated. The residue was mixed with $H_2O$ (200 ml) and extracted with $CH_2Cl_2$ (2×100 ml, 2×50 ml). The combined organic phases were washed with saturated NaCl solution (2×100 ml), dried ($Na_2SO_4$) and evaporated, giving 0.76 g of a brown oil. The two products were separated and purified through MPLC (p=4 bar, silica gel 60, $CH_2Cl_2$/MeOH 10:2). Then they were dissolved in a little MeOH and converted into the dihydrochlorides using ethereal HCl. Since no crystallisation of 22.2 HCl occurred, the solvent was drawn off, the residue dissolved in $H_2O$ and freeze dried. The mother liquor of 23.2 HCl was also evaporated, the residue dissolved in $H_2O$ and freeze dried.

Compound 22.2 HCl: Yield: 0.20 g (8%) of yellow lyophilisate: IR (KBr): 3423 (OH), 1743 (C=O) cm$^{-1}$; $^1$H-NMR (DMSO-d$_6$): δ 9.81, 9.50, 9.34 (3 s, 4 H, OH, NH$^+$, NH$_2^+$), 6.81 (d, J=8.1, 1 arom. H); 6.64 (d, J=8.1, 1 arom. H); 4.50 (d, J=3.6, H—C(5)); 4.23 (q, J=6.9, —COOCH$_2$CH$_3$); 3.13 (s, CH$_3$O—C(14)); 2.88 (d, J=4.4, CH$_3$N); 1.26 (t, J=6.9, —COOCH$_2$CH$_3$).

Compound 23.2 HCl: Yield: 0.20 g (8%) of white crystals (0.11 g) and yellow lyophilisate (0.09 g): Fp>200° C. (Brkd.); IR (KBr): 3413 (OH), 1745 (C=O) cm$^{-1}$; $^1$H-NMR (DMSO-d$_6$): δ 10.02, 9.61, 9.51 (3 s, 4 H, OH, NH$^+$, NH$_2^+$), 6.82 (d, J=8.0, 1 arom. H); 6.70 (d, J=8.0, 1 arom. H); 4.95 (d, J=7.4, H—C(5)); 4.22 (q, J=7.0, —COOCH$_2$CH$_3$); 3.26 (s, CH$_3$O—C(14)); 2.85 (s, CH$_3$N); 1.25 (t, J=7.0, —COOCH$_2$CH$_3$).

EXAMPLE 20

Synthesis of (4,5α-epoxy-3-hydroxy-14β-ethoxy-17-methylmorphinan-6α-ylamino)-acetic acid-tert.-butylester (Compound 24) and (4,5α-epoxy-3-hydroxy-14β-ethoxy-17-methylmorphinan-6β-ylamino)-acetic acid-tert.-butylester (Compound 25)

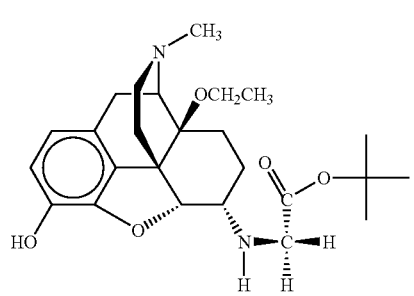

Verbindung 24

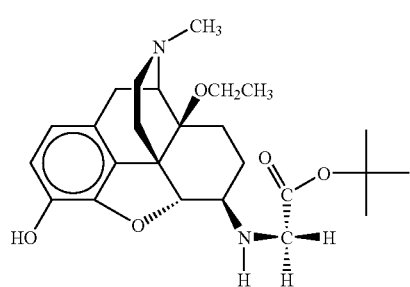

Verbindung 25

A mixture of 14-O-ethyloxymorphone (H. Schmidhammer, R. Krassnig, Sci. Pharm. 1990, Vol. 58, pp. 255-257) (1.02 g, 3.09 mmol), glycine-tert.-butylester hydrochloride (0.7 g, 4.63 mmol), absolute EtOH (100 ml), N-ethyldiisopropylamine (0.9 ml, 5.0 mmol) and molecular sieve (2 g) was stirred for 3 h under N$_2$ at room temperature. Then a solution of NaCNBH$_3$ (0.25 g, 3.98 mmol) in ethanol (20 ml) was added drop by drop and the solution stirred further under N$_2$ at room temperature. After 2 days H$_2$O (5 ml) was added, filtered through Celite and the mixture evaporated. The residue was mixed with H$_2$O (150 ml) and extracted with Et$_2$O (2×100 ml, 1×80 ml, 2×50 ml). The combined organic phases were washed with saturated NaCl solution (3×100 ml), dried (Na$_2$SO$_4$) and evaporated. The aqueous phase was extracted with CH$_2$Cl$_2$/i-PrOH 4:1 (2×100 ml). The combined organic phases were treated in the same manner as for the ether phase described above. From the 1st extraction (Et$_2$O) 1.05 g of a yellow foam resin was obtained and from the 2nd extraction (CH$_2$Cl$_2$/i-PrOH) 0.17 g of a white foam resin. The two products were separated and purified through MPLC (p=5 bar, silica gel 60, CH$_2$Cl$_2$/MeOH 10:1).

Compound 24: Yield: 0.09 g (7%) of white foam resin: IR (KBr): 3425 (OH), 1735 (C=O) cm$^-$; $^1$H-NMR (CDCl$_3$): δ 6.66 (d, J=8.0, 1 arom. H); 6.47 (d, J=8.0, 1 arom. H); 4.68 (d, J=2.6, H—C(5)); 3.43 (s, C(6)-NH—CH$_2$—); 2.32 (s, CH$_3$N); 1.45 (s, —COOC(CH$_3$)$_3$); 1.15 (t, J=7.0, C(14)-OCH$_2$CH$_3$); Cl-MS: m/z 445 (M$^+$+1).

Compound 25: Yield: 0.19 g (14%) of white foam resin IR (KBr): 3440 (OH), 1734 (C=O) cm$^{-1}$; $^1$H-NMR (CDCl$_3$): δ 6.67 (d, J=8.0, 1 arom. H); 6.53 (d, J=8.0, 1 arom. H); 4.48 (d, J=7.0, H—C(5)); 3.50 (d, J=17.2, 1 H, C(6)-NH—CH$_2$—); 3.23 (d, J=17.2, 1 H, C(6)-NH—CH$_2$—); 2.33 (s, CH$_3$N); 1.44 (s, —COOC(CH$_3$)$_3$); 1.19 (t, j=7.0, C(14)-OCH$_2$CH$_3$); Cl-MS: m/z 445 (M$^+$+1).

EXAMPLE 21

Synthesis of (4,5α-epoxy-3-hydroxy-14β-ethoxy-17-methylmorphinan-6α-ylamino)-acetic acid bis(tetrafluoroborate) (Compound 26.2 HBF$_4$)

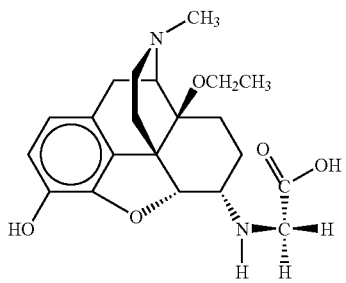

Verbindung 26

A solution of Compound 24 (0.05 g, 0.11 mmol) in CH$_2$Cl$_2$ (3 ml) was mixed with 54% tetrafluoroboric acid (HBF$_4$) in Et$_2$O (0.08 ml) and the mixture subjected to ultrasound for 15 min. at room temperature. Then the resulting precipitate was filtered off and dried. Yield: 0.03 g (53%) of white 3.2 HBF$_4$: Fp>286° C. (Brkd.); IR (KBr): 3466 (OH), 1735 (C=O), 1067 (B—F) cm$^{-1}$; $^1$H-NMR (D$_2$O): δ 6.90 (d, J=8.0, 1 arom. H); 6.81 (d, J=8.0, 1 arom. H); 5.07 (d, J=3.6, H—C(5)); 4.02 (s, C(6)-NH—CH$_2$—); 2.96 (s, CH$_3$N); 1.24 (t, J=7.0, C(14)-OCH$_2$CH$_3$); ESI-MS: m/z 389 (M$^+$+1).

EXAMPLE 22

Synthesis of (4,5α-epoxy-3-hydroxy-14β-ethoxy-17-methylmorphinan-6β-ylamino)-acetic acid bis(tetrafluoroborate) (Compound 27.2 HBF$_4$)

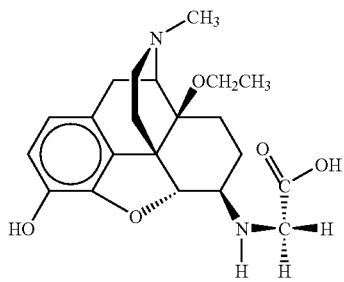

Compound 27

Verbindung 27

A solution of Compound 25 (0.10 g, 0.22 mmol) in CH$_2$Cl$_2$ (6 ml) was mixed with 54% tetrafluoroboric acid (HBF$_4$) in Et$_2$O (0.16 ml) and the mixture subjected to ultrasound for 15 min. at room temperature. Then the resulting precipitate was filtered off and dried. Yield: 0.09 g (73%) of white 3.2 HBF$_4$: Fp>280° C. Brkd.); IR (KBr): 3426 (OH), 1758 (C=O), 1064 (B—F) cm$^{-1}$; $^1$H-NMR (D$_2$O): δ 6.90 (d, J=8.0, 1 arom. H); 6.85 (d, J=8.0, 1 arom. H); 4.92 (d, J=7.6, H—C(5)); 4.03 (s, C(6)-NH—C$\underline{H}_2$—); 2.94 (s, CH$_3$N); 1.29 (t, J=6.8, C(14)-OCH$_2$CH$_3$); ESI-MS: m/z 389 (M$^+$+1).

EXAMPLE 23

Synthesis of (2'S)-2'-(17-cyclopropylmethyl-4,5α-epoxy-3,14β-dihydroxymorphinan-6β-ylamino)-3-phenylpropionic acid-tert.-butylester (Compound 28)

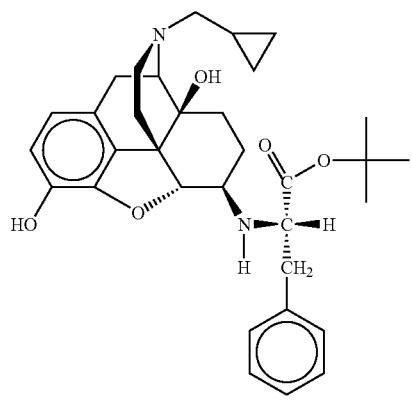

Compound 28

Verbindung 28

A mixture of naltrexone hydrochloride (Brit. Patent GB 1119270, 1968) (5.46 g, 13.23 mmol), L-phenylalanine-tert.-butylester hydrochloride (5.46 g, 21.18 mmol), absolute EtOH (250 ml), N-ethyldiisopropylamine (6 ml, 43.4 mmol) and molecular sieve (5 g) was stirred for 6 h under N$_2$ at room temperature. Then NaCNBH$_3$ (0.91 g, 14.48 mmol) was added and the solution stirred further under N$_2$ at room temperature. After 6 days H$_2$O (20 ml) was added, filtered and the filtrate evaporated. The residue was mixed with H$_2$O (300 ml), alkalized with conc. ammonia and extracted with CH$_2$Cl$_2$ (1×100 ml, 4×50 ml). The combined organic phases were washed with H$_2$O (2×200 ml), dried (Na$_2$SO$_4$) and evaporated. From the evaporation residue (8.44 g) 2 g were purified using circular chromatography (silica gel 60, CH$_2$Cl$_2$/MeOH/conc. ammonia of 250:1:0.1 to 150:2.5:0.2). Yield 0.33 g (19% referred to the complete raw product) of pure 28 as white foam resin: $^1$H-NMR (DMSO-d$_6$): δ 8.98 (s, OH—C(3)), 7.22 (m, 5 arom. H), 6.56 (d, J=8.0, 1 arom. H); 6.46 (d, J=8.0, 1 arom. H); 4.78 (s, OH—C(14)); 4.14 (d, J=6.0, H—C(5)); 1.20 (s, —COOC(C$\underline{H}_3$)$_3$); 0.84 (m, CH (cyclopropyl)); 0.47 (m, CH$_2$ (cyclopropyl)); 0.09 (m, CH$_2$ (cyclopropyl)); Cl-MS: m/z 547 (M$^+$+1).

EXAMPLE 24

Synthesis of (2'S)-2'-(17-cyclopropylmethyl-4,5α-epoxy-3,14β-dihydroxymorphinan-6β-ylamino)-3-phenylpropionic acid bis(tetrafluoroborate) (Compound 29.2 HBF$_4$)

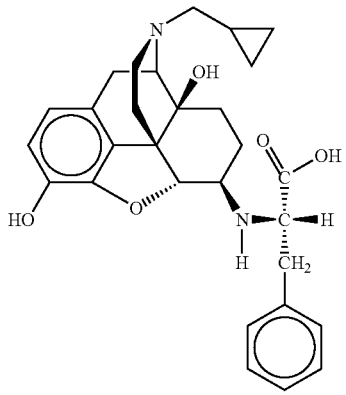

Compound 29

Verbindung 29

A solution of Compound 28 (0.18 g, 0.33 mmol) in CH$_2$Cl$_2$ (5 ml) was mixed with 54% tetrafluoroboric acid (HBF$_4$) in Et$_2$O (0.22 ml) and the mixture was stirred for 1 h at 0° C. The resulting precipitate was filter off and dried. The raw product was purified by circular chromatography (silica gel 60, CH$_2$Cl$_2$/MeOH from 7:3 to 3:7, then MeOH alone). Yield 0.06 g (27%) of pure 29.2 HBF$_4$ as yellow foam resin. $^1$H-NMR (DMSO-d$_6$): δ 7.17 (m, 5 arom. H), 6.45 (d, J=8.2, 1 arom. H); 6.35 (d, J=8.2, 1 arom. H); 4.73 (s, OH—C(14)); 4.08 (d, J=7.4, H—C(5)); 0.80 (m, CH (cyclopropyl)); 0.44 (m, CH$_2$ (cyclopropyl)); 0.09 (m, CH$_2$ (cyclopropyl)); HR-FAB-MS: m/z calculated for C$_{29}$H$_{35}$N$_2$O$_5$ (M$^+$+1): 491.2536. Found 491.2540.

EXAMPLE 25

Synthesis of 3-benzyloxy-17-cyclopropylmethyl-4,5α-epoxy-14β-hydroxy-morphinan-6-spiro-2'-1,3-dioxolane (Compound 30)

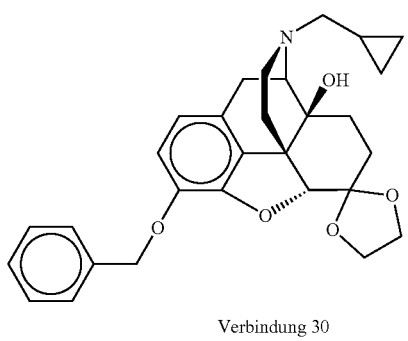

Verbindung 30

A mixture of 17-cyclopropyl-4,5α-epoxy-3,14 β-dihydroxymorphinan-6-spiro-2'-dioxolane (H.Schmidhammer et al., Heterocycles 1998, Vol. 49, pp. 489-497) (6.90 g, 17.90 mmol), $K_2CO_3$ (6.70 g, 48.48 mmol), benzylbromide (2,34 ml, 19.66 mmol) and absolute DMF (70 ml) was stirred for 21 h under $N_2$ at room temperature. The inorganic material was filtered off, rinsed with $CH_2Cl_2$ and the filtrate evaporated. The residue (yellow coloured crystals) was recrystallised out of MeOH. Yield 7.37 g (87%) of pure 30 as yellow crystals. Fp 130-131° C.; IR (KBr): 3352 (OH) $cm^{-1}$; $^1$H-NMR ($CDCl_3$): δ 7.42-7.27 (m, 5 arom. H); 6.75 (d, J=8.3, 1 arom. H); 6.54 (d, J=8.3, 1 arom. H); 5.17 (d, J=11.7, $OCH_2Ph$), 5.10 (d, J=11.7, $OCH_2Ph$), 4.58 (s, H—C(5)); 4.19-3.73 (m, C(6)-O—$CH_2$—$CH_2$—O—C(6)); Cl-MS: m/z 476 ($M^+$+1).

EXAMPLE 26

Synthesis of 3-benzyloxy-17-cyclopropylmethyl-4,5α-epoxy-14β-{[(E)-3-phenylprop-2-enyl]oxy}morphinan-6-spiro-2'-1,3-dioxolane hydrochloride (Compound 31.HCl)

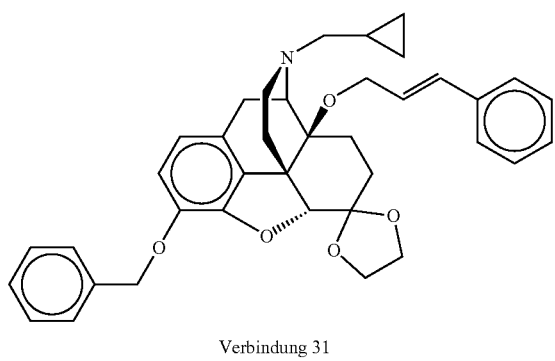

Verbindung 31

A mixture of Compound 30 (4.00 g, 8.41 mmol), absolute DMF (50 ml), NaH (0.60 g, 25.23 mmol, from 1.00 g of 60% NaH dispersion through multiple washing with petrolether) was stirred for 20 min. under $N_2$ at 0° C. Then a solution of cinnamyl bromide (2.15 g, 10.93 mmol) in DMF (20 ml) was added drop by drop and the mixture stirred further for 3 h at room temperature under $N_2$. After the decomposition of the excess NaH by the careful addition of small pieces of ice, the mixture was poured onto 400 ml of $H_2O$ and extracted with $CH_2Cl_2$ (4×75 ml). The combined organic phases were washed with $H_2O$ (5×300 ml) and saturated NaCl solution (1×100 ml), dried ($Na_2SO_4$) and evaporated. The evaporation residue (5.25 g orange coloured oil) was purified by column chromatography (silica gel 60, $CH_2Cl_2$/MeOH/conc. ammonia 250:2:0.5). Yield 1.86 g (37%) of pure 31. For analytical purposes 0.2 g were dissolved in ether and 31.HCl precipitated as ochre coloured powder by the addition of ethereal HCl. Fp 133-136° C.; $^1$H-NMR (DMSO-$d_6$): δ 8.33 (br s, $NH^+$); 7.53-7.24 (m, 10 arom. H); 6.93 (d, J=8.4, 1 arom. H); 6.72-6.68 (m, 1 arom. H, 2 olef. H); 5.15 (s, $OCH_2Ph$); 4.65 (s, H—C(5)); 4.31-4.21 (m, C(6)-O—$CH_2$—$CH_2$—O—C(6)); 1.09 (m, CH (cyclopropyl)); 0.72-0.44 (m, 2×$CH_2$ (cyclopropyl)); Cl-MS: m/z 592 ($M^+$+1).

EXAMPLE 27

Synthesis of 17-cyclopropylmethyl-4,5α-epoxy-3-hydroxy-14β-[3-(phenylpropyl)oxy]morphinan-6-spiro-2'-1,3-dioxolane hydrochloride (Compound 32.HCl)

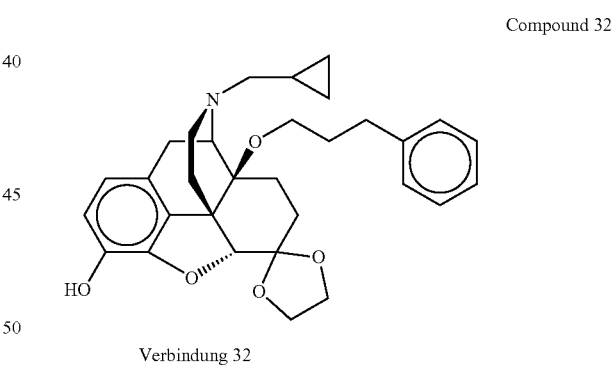

Verbindung 32

A mixture of 31 (0.89 g, 1.51 mmol), MeOH (50 ml), THF (15 ml) and 10% Pd/C (90 mg) was hydrogenated at room temperature and 30 psi for 2 h. Then the catalyst was filtered off and the filtrate evaporated. The evaporation residue (1.0 g of yellow oil) was purified by column chromatography (silica gel 60, $CH_2Cl_2$/MeOH/conc. ammonia 250:5:0.5). Yield 0.41 g (53%) of pure 32. For analytical purposes 70 mg were dissolved in ether and 32.HCl precipitated as a white powder by the addition of ethereal HCl. Fp 158-162° C.; $^1$H-NMR (DMSO-$d_6$): δ 9.24 (s, OH); 7.79 (br, s, $NH^+$); 7.35-7.19 (m, 5 arom. H); 6.68 (d, J=8.0, 1 arom. H); 6.57 (d, J=8.0, 1 arom. H); 4.51 (s, H—C(5)); 4.31-4.21 (m, C(6)-O—$CH_2$—$CH_2$—O—C(6)); Cl-MS: m/z 504 ($M^+$+1).

EXAMPLE 28

Synthesis of 17-cyclopropylmethyl-4,5α-epoxy-3-hydroxy-14β-[3-(phenylpropyl)oxy]morphinan-6-on hydrochloride (Compound 33.HCl)

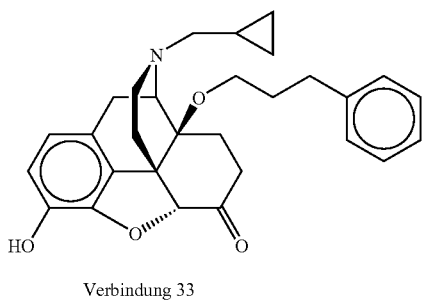

Verbindung 33

A solution of 32 (4.00 g, 7.94 mmol) in 28 ml of MeOH and 12 ml of conc. HCl was reflux heated for 1.5 h, then poured over 100 ml of ice/water and alkalized with conc. ammonia. The mixture was extracted with $CH_2Cl_2$ (4×100 ml), the combined organic phases washed with water (2×100 ml) and saturated NaCl solution (2×100 ml), dried ($Na_2SO_4$) and evaporated. The evaporation residue (3.98 g of brown oil) was purified by column chromatography (silica gel 60, $CH_2Cl_2$/MeOH/conc. ammonia 250:3:0.5). Yield 3.05 g (83%) of pure 33. For analytical purposes 90 mg were dissolved in ether and 33.HCl precipitated as colourless crystals by the addition of ethereal HCl. Fp 220-230° C.; $^1$H-NMR (DMSO-$d_6$): δ 9.52 (s, OH); 8.20 (s, $NH^+$); 7.30-7.18 (m, 5 arom. H); 6.71 (d, J=8.0, 1 arom. H); 6.64 (d, J=8.0, 1 arom. H); 4.89 (s, H—C(5)); Cl-MS: m/z 460 ($M^+$+1).

EXAMPLE 29

Synthesis of {17-cyclopropylmethyl-4,5α-epoxy-3-hydroxy-14β-[(3-phenylpropyl)oxy]-morphinan-6α-ylamino}-acetic acid-tert.-butylester (Compound 34) and {17-cyclopropylmethyl-4,5α-epoxy-3-hydroxy-14β-[(3-phenylpropyl)oxy]-morphinan-6β-ylamino}-acetic acid-tert.-butylester (Compound 35)

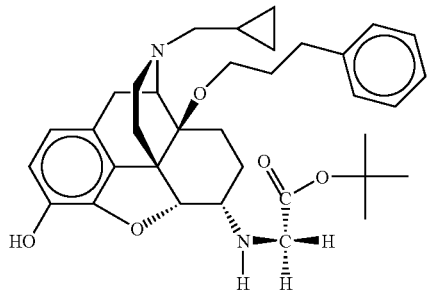

Verbindung 34

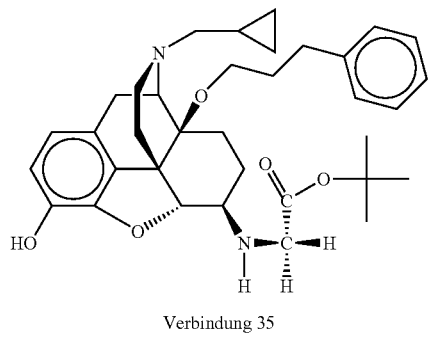

Verbindung 35

A mixture of Compound 33 (0.7 g, 1.41 mmol), glycine-tert.-butylester hydrochloride (0.26 g, 1.55 mmol), absolute EtOH (20 ml), triethylamine (0.49 ml, 3.53 mmol) and molecular sieve (0.7 g) was stirred for 23 h at room temperature under $N_2$. Then $NaCNBH_3$ (0.13 g, 2.07 mmol) was added and the solution stirred further under $N_2$ at room temperature. After 3 days $H_2O$ (5 ml) was added, filtered and the filtrate evaporated. The residue was mixed with $H_2O$ (20 ml), alkalized with conc. ammonia and extracted with $CH_2Cl_2$ (1×50 ml, 3×30 ml). The combined organic. phases were washed with saturated NaCl solution (3×200 ml), dried ($Na_2SO_4$) and evaporated. The evaporation residue (0.62 g of brown oil) was separated and purified by column chromatography (silica gel 60, $CH_2Cl_2$/MeOH/conc. ammonia 250:2:0.5).

Compound 34: Yield 70 mg (9%). $^1$H-NMR (CDCl$_3$): δ 7.28-7.16 (m, 5 arom. H); 6.67 (d, J=8.1, 1 arom. H); 6.45 (d, J=8.1, 1 arom. H); 4.70 (d, J=3.4, H—C(5)); 1.44 (s, —COOC(C$\underline{H}_3$)$_3$); Cl-MS: m/z 575 ($M^+$+1).

Compound 35: Yield 40 mg (5%). $^1$H-NMR (DMSO-$d_6$): δ 8.96 (s, OH); 7.31-7.16 (m, 5 arom. H); 6.54 (d, J=8.3, 1 arom. H); 6.45 (d, J=8.3, 1 arom. H); 4.25 (d, J=6.6, H—C(5)); 1.39 (s, —COOC(C$\underline{H}_3$)$_3$); Cl-MS: m/z 575 ($M^+$+1).

EXAMPLE 30

Synthesis of (2'S)-2'-(17-cyclopropylmethyl-4,5α-epoxy-3-hydroxy-14β-[(3-phenylpropyl)oxy]-morphinan-6α-ylamino)-3-phenylpropionic acid-tert.-butylester (Compound 36) and (2'S)-2'-(17-cyclopropylmethyl-4,5α-epoxy-3-hydroxy-14β-[(3-phenylpropyl)oxy]-morphinan-6β-ylamino)-3-phenylpropionic acid-tert.-butylester (Compound 37)

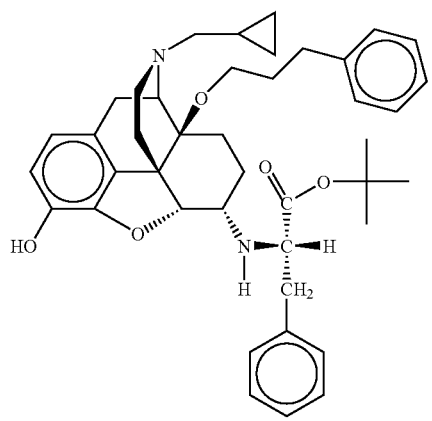

Verbindung 36

-continued

Compound 37

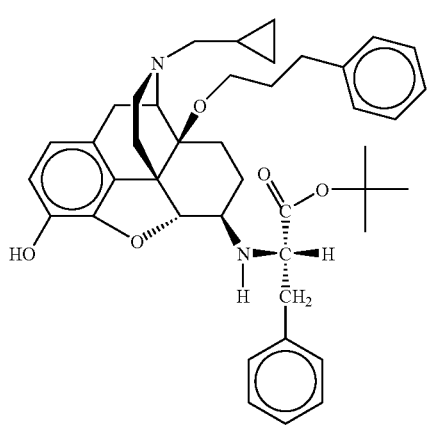

Verbindung 37

A mixture of Compound 33 (0.7 g, 1.41 mmol), L-phenylalanine-tert.-butylester hydrochloride (0.55 g, 2.13 mmol), absolute EtOH (20 ml), triethylamine (0.49 ml, 3.53 mmol) and molecular sieve (0.7 g) was stirred for 23 h at room temperature under $N_2$. Then $NaCNBH_3$ (0.13 g, 2.07 mmol) was added and the solution stirred further under $N_2$ at room temperature. After 4 days $H_2O$ (5 ml) was added, filtered and the filtrate evaporated. The residue was mixed with $H_2O$ (20 ml), alkalized with conc. ammonia and extracted with $CH_2Cl_2$ (1×50 ml, 3×30 ml). The combined organic phases were washed with saturated NaCl solution (3×100 ml), dried ($Na_2SO_4$) and evaporated. The evaporation residue (brown oil) was separated and purified by column chromatography (silica gel 60, $CH_2Cl_2$/MeOH/conc. ammonia 250:2:0.5).

Compound 36: Yield 70 mg (7%). $^1$H-NMR (DMSO-$d_6$): δ 8.90 (s, OH); 7.31-7.12 (m, 5 arom. H); 6.56 (d, J=8.2, 1 arom. H); 6.40 (d, J=8.2, 1 arom. H); 4.52 (d, J=3.6, H—C(5)); 1.22 (s, —COOC(C$\underline{H}_3$)$_3$); Cl-MS: m/z 665 (M$^+$+1).

Compound 37: Yield 0.33 g (35%). $^1$H-NMR (DMSO-$d_6$): δ 8.98 (s, OH); 7.27-7.13 (m, 5 arom. H); 6.54 (d, J=8.0, 1 arom. H); 6.44 (d, J=8.0, 1 arom. H); 4.21 (d, J=7.0, H—C (5)); 1.20 (s, —COOC(C$\underline{H}_3$)$_3$); Cl-MS: m/z 665 (M$^+$+1).

EXAMPLE 31

Synthesis of {17-cyclopropylmethyl-4,5α-epoxy-3-hydroxy-14β-[(3-phenylpropyl)oxy]-morphinan-6β-ylamino}acetic acid dihydrochloride (Compound 38.2 HCl)

Compound 38

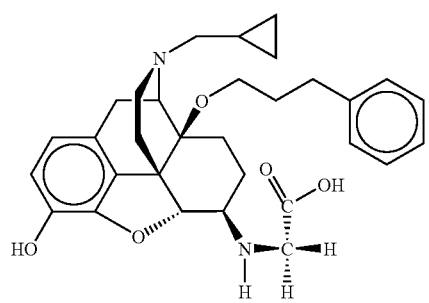

Verbindung 38

A mixture of Compound 35 (40 mg, 0.07 mmol) and 4 M HCl in dioxane (2 ml) was reflux heated for 6 h. The precipitate was filtered off and dried. Yield 10 mg (24%) of white 38.2 HCl: $^1$H-NMR (D$_2$O): δ 7.38-7.26 (m, 5 arom. H); 6.89 (d, J=8.0, 1 arom. H); 6.83 (d, J=8.0, 1 arom. H); 4.91 (d, J=7.4, H—C(5)); 4.00 (s, C(6)-NH—C$\underline{H}_2$—).

EXAMPLE 32

Opioid Receptor Binding Studies

Opioid receptor binding studies were carried out on rat's brain homogenisates using [$^3$H]DAMGO (μ-receptor agonist) as radio-ligand and with strict conformance to an earlier publication (M. Spetea et al., Neurochemical Research 1998, Vol. 23, pp. 1213-1218).

The compounds 1-4, 7, 8, 11, 16, 17, 22, 23 and 38 indicate very high affinity to μ-opioid receptors, which are principally responsible for analgesia (Table 1). In comparison to them, morphine clearly indicates lower affinity to μ-opioid receptors.

TABLE 1

Opioid receptor binding studies of the compounds 1-4, 7, 8, 11, 16, 17, 22, 23 and 38 and morphine.

| Compound | $K_i$ (nM) (μ-receptors) |
| --- | --- |
| 1 | 0.48 |
| 2 | 1.30 |
| 3 | 0.90 |
| 4 | 0.83 |
| 7 | 0.77 |
| 8 | 1.90 |
| 11 | 0.95 |
| 16 | 0.61 |
| 17 | 0.25 |
| 22 | 0.21 |
| 23 | 0.80 |
| 38 | 0.24 |
| Morphine | 6.55 |

EXAMPLE 33

Analgesia Test

A test on rats was applied ("rat tail flick test"). This test was carried out as previously described (Zs. Fürst et al., Eur. J. Pharmacol. 1993, Vol. 236, pp. 209-215).

The compounds 3, 4, 7 and 8 showed a very high analgesic activity. Compound 4 is 68 times as active as morphine after subcutaneous application (sc) and 238 times as active as morphine after intracerebroventricular application (icv) (Table 2). The high sc/icv ratio figures of Compounds 3, 4, 7 and 8 show that in comparison to morphine these compounds are preferentially distributed in the periphery and also preferentially develop their analgesic effect in the periphery. This means from these figures that Compound 3 can only overcome the blood-brain barrier in a very restricted manner and its effectiveness is therefore primarily evident in the periphery (outside of the central nervous system). This fits in with a very low rate of side effects, which relates to central side effects, such as for example, nausea, vomiting, sedation, dizziness, confusion, respiratory depression and mania.

The Compounds 3 and 4 indicate a substantially longer analgesic effective period than morphine. Whereas the Compounds 3 (0.5 μg/rat) and 4 (0.25 μg/rat) still showed 100% analgesic activity after 120 minutes the activity of morphine (50 μg/rat) sinks to 20% after 120 minutes (Table 3). The compounds 3 and 4 still have 90% of the analgesic activity after 180 minutes.

TABLE 2

"Rat tail flick test" for compounds 3, 4, 7, 8 and morphine.

| Compound | $ED_{50}$ (µg/kg, sc[a]) | $ED_{50}$ (µg/kg, icv[b]) | sc/icv |
|---|---|---|---|
| 3 | 86 | 0.49 | 176 |
| 4 | 28 | 0.42 | 67 |
| 7 | 100 | 0.75 | 133 |
| 8 | 500 | 0.67 | 746 |
| Morphine | 1900 | 100 | 19 |

[a]sc = subcutaneous application.
[b]icv = intracerebroventricular application.

TABLE 3

Analgesic effect (in percent) of the Compounds 3, 4 and morphine after 10, 20, 30, 60, 120 and 180 minutes in the "Rat tail flick test" after intracerebroventricular application.

| Compound (µg/rat[a]) | 10 | 20 | 30 | 60 | 120 | 180 minutes |
|---|---|---|---|---|---|---|
| 3 (0.5) | 46 | 62 | 59 | 100 | 100 | 90 |
| 4 (0.25) | 61 | 74 | 76 | 100 | 100 | 90 |
| Morphine (50) | 57 | 91 | 74 | 59 | 20 | ND[b] |

[a]The weight of the rats used was in each case 120 g.
[b]ND = Not determined.

EXAMPLE 34

Randall-Selitto Test

The Randall-Selilto Test (L. O. Randall and J. J. Selitto, Arch. Int. Pharmacodyn. 1957, Vol.111, pp. 409-419) was applied to study the analgesic effect on carrageen-induced hyperalgesia on the right hind paw of rats. In this way the "hind-paw withdrawal latency" (HWL; latency period for withdrawing the right hind paw) with mechanical stimulation (e.g. I. Bileviciute-Ljungar and M. Spetea, Br. J. Pharmcol. 2001, Vol. 132, pp. 252-258) is measured.

The Compounds 4 and the centrally effective reference substance, 14-methoxymetopone (Zs. Fürst et al., Eur. J. Pharmacol. 1993, Vol. 236, pp. 209-215), both show significant analgesic activity at a dosage in each case of 20 µg/kg after subcutaneous application (a rise in the latency period for withdrawal of the hind paw (HWL) of at least 100% is taken as being significant analgesic activity). Whereas Compound 4 shows a long lasting effect (approx. 14 hours), the effect of 14-methoxymetopone is substantially shorter at 2 hours.

The exclusively peripheral analgesic effect of Compound 4 was proved by the following test. The analgesic effect of Compound 4 (20 µg/kg) was completely neutralised by subcutaneous application of the selectively peripherally acting opioid antagonist naloxone methiodide (an equivalent), whereas the analgesic effect of the 14-methoxymetopone (20 µg/kg) through subcutaneous application of the selectively peripherally acting opioid antagonist naloxone methiodide (an equivalent) was not affected. This is proof that the analgesic effect of Compound 4 is passed via peripheral opioid receptors, whereas the analgesic effect of the 14-methoxymetopone is passed via opioid receptors of the central nervous system. This leads to the conclusion that Compound 4 cannot overcome the blood-brain barrier and therefore cannot show any side effects passed through the central nervous system (e.g. respiratory depression, dizziness, confusion, sedation, sleepiness, mania).

EXAMPLE 35

Respiratory Depression Test in Rats

In this test the respiratory volume and the frequency of respiration of anaesthetised rats was measured.

The Compounds 3 and 4 were examined for their property of being able to cause a respiratory depression (see Table 4). With subcutaneous application (sc) of the Compounds 3 and 4 very high doses were necessary to cause a respiratory depression. Since with intracerebroventricular application (icv) a respiratory depression is caused with substantially lower dosages, very high sc/icv ratios (1205 resp. 1190) result for Compounds 3 and 4. The sc/icv ratios for morphine and fentanyl are noticeably lower (34 resp. 0.2).

Whereas the analgesic $ED_{50}$ values ("rat tail flick test") are very similar to the $ED_{50}$ values of the respiratory depression test after intracerebroventricular application, these values are very different after subcutaneous application. If the high $ED_{50}$ values of the respiratory depression test after subcutaneous application of 3 and 4 are compared with the low $ED_{50}$ values of the "rat tail flick test" after subcutaneous application, then it can be seen that for Compound 3 a 12 times higher dose is necessary than the analgesic dose in order to initiate respiratory depression. In the case of Compound 4 a dose 18 times higher is required. Analgesic doses of the Compounds 3 and 4 are therefore not able to initiate a respiratory depression.

TABLE 4

"Respiratory depression tests in rats" for the Compounds 3, 4, morphine and fentanyl.

| Compound | $ED_{50}$ (µg/kg, sc[a]) | $ED_{50}$ (µg/kg, icv[b]) | sc/icv |
|---|---|---|---|
| 3 | 1000 | 0.83 | 1205 |
| 4 | 500 | 0.42 | 1190 |
| Fentanyl | 25 | 125 | 0.2 |
| Morphine | 2800 | 83 | 34 |

[a]sc = subcutaneous application.
[b]icv = intracerebroventricular application.

EXAMPLE 36

Determination of the Antiallodynic Effect

Two tests were carried out on rats:
a) Von Frey test (mechanical allodynia)
b) Cold water allodynia test (thermal allodynia)

The tests involve models to test the effect of a substance on neuropathic pain. For both tests ligations were applied around the ischias nerve (G. J. Bennett and Y. K. Xie, Pain 1988, Vol. 33, 87-107).

a) Von Frey test (mechanical allodynia)

A slight pressure (2 to 60 g) was exerted on the skin of the hind paw of the rats (200-250 g) using Von Frey hairs and the latency period of withdrawal of the hind paw was studied at various time intervals (5, 15, 30 and 60 minutes after the application of the substance). The substance to be investigated was applied via intraplant (ipl).

The Compound 4 shows significant anti-allodynic activity at a dosage of 100 µg/rat after subcutaneous application (a rise of at least 100% in the latency period of the withdrawal of the hind paw is taken as significant anti-allodynic activity). The peripherally acting opioid antagonist naloxone methiodide (ipl) was able to completely neutralise the anti-allodynic effect of Compound 4.

b) Cold water allodynia test (thermal allodynia)

Thermal stimulation (cold water) was used to initiate withdrawal of the hind paw of the rats (200-300 g). After 5, 15 and 30 min (after application of the substance) the latency period of the withdrawal of the hind paw was studied (J. C. Hunter et al., Eur. J. Pharmacol., 1997, Vol. 324, 153-160). The substances to be investigated were applied via intraplant (ipl).

The Compound 4 shows significant anti-allodynic activity at a dosage of 100 μg/rat after subcutaneous application (a rise of at least 100% in the latency period of the withdrawal of the hind paw is taken as significant anti-allodynic activity). The peripherally acting opioid antagonist naloxone methiodide (ipl) was able to completely neutralise the anti-allodynic effect of Compound 4.

The invention claimed is:

1. A Compound of formula (I),

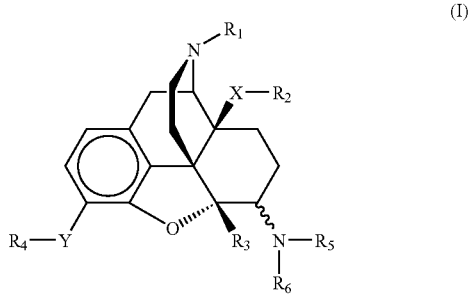

in which the substituents have the following meaning:

$R_1$ is hydrogen; $C_1$-$C_6$-alkyl; $C_2$-$C_6$-alkenyl; $C_2$-$C_6$-alkinyl; $C_1$-$C_6$-monohydroxyalkyl; $C_2$-$C_6$-dihydroxyalkyl; $C_3$-$C_6$-trihydroxyalkyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl;

the nitrogen joined with $R_1$ can also be quartenised by two substituents $R_1$, which can be the same or different and which are defined as previously shown, and whereby the second, quarternised substituent can additionally have the meaning hydroxyl, oxyl (N oxide) as well as alkoxyl;

$R_2$ is $C_1$-$C_6$-alkyl; $C_1$-$C_6$-monohydroxyalkyl; $C_2$-$C_6$-dihydroxyalkyl; $C_3$-$C_6$-trihydroxyalkyl; $C_2$-$C_6$-alkenyl; $C_2$-$C_6$-alkinyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl; $C_2$-$C_6$-alkanoyl; $C_3$-$C_6$-alkenoyl; $C_3$-$C_6$-alkinoyl; $C_7$-$C_{16}$-arylalkanoyl, where aryl is $C_6$-$C_{10}$-aryl and alkanoyl is $C_1$-$C_6$-alkanoyl; $C_9$-$C_{16}$-arylalkenoyl, where aryl is $C_6$-$C_{10}$-aryl and alkenoyl is $C_3$-$C_6$-alkenoyl; $C_9$-$C_{16}$-arylalkinoyl, where aryl is $C_6$-$C_{10}$-aryl and alkinoyl is $C_3$-$C_6$-alkinoyl;

$R_3$ is hydrogen; $C_1$-$C_6$-alkyl; $C_2$-$C_6$-alkenyl; $C_7$-$C_{16}$-arylalkyl where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; alkoxyalkyl, where alkoxy is $C_1$-$C_6$-alkoxy and alkyl is $C_1$-$C_6$-alkyl; $CO_2(C_1$-$C_6$-alkyl); $CO_2H$; $CH_2OH$;

$R_4$ is hydrogen; $C_1$-$C_6$-alkyl; $C_2$-$C_6$-alkenyl; $C_2$-$C_6$-alkinyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl; $C_2$-$C_6$alkanoyl; $C_3$-$C_6$-alkenoyl; $C_3$-$C_6$-alkinoyl; $C_7$-$C_{16}$-arylalkanoyl, where aryl is $C_6$-$C_{10}$-aryl and alkanoyl is $C_1$-$C_6$-alkanoyl; $C_9$-$C_{16}$-arylalkenoyl, where aryl is $C_6$-$C_{10}$-aryl and alkenoyl is $C_3$-$C_6$-alkenoyl; $C_9$-$C_{16}$-arylalkinoyl, where aryl is $C_6$-$C_{10}$-aryl and alkinoyl is $C_3$-$C_6$-alkinoyl; iminomethyl, formanidinyl, $C_1$-$C_6$-N-alkyl- and N,N'-dialkylformamidinyl; $C_2$-$C_6$-N-alkenyl- and N,N'-dialkenylformamidinyl; $C_2$-$C_6$-N-alkinyl- and N,N'-dialkinylformamidinyl; $C_4$-$C_{16}$-N-cycloalkylalkyl- and N,N'-dicycloalkylalkylformamidinyl, where cycloalkyl is $C_3$-$C_{10}$-cycloalkyl and alkyl is $C_1$-$C_6$-alkyl; $C_5$-$C_{16}$-N-cylcoalkylalkenyl- and N,N'-dicycloalkylalkenylformamidinyl where cycloalkyl is $C_3$-$C_{10}$-cycloalkyl and alkenyl is $C_2$-$C_6$-alkenyl; $C_5$-$C_{16}$-N-cycloalkylalkinyl- and N,N'-dicycloalkylalkinylformamidinyl, where cycloalkyl is $C_3$-$C_{10}$-cycloalkyl and alkinyl is $C_2$-$C_6$-alkinyl; $C_7$-$C_{16}$-N-arylalkyl- and N,N'-diarylalkylformamidinyl, where aryl is $C_6$-$C_{10}$-aryl and alkyl is $C_1$-$C_6$-alkyl;

$R_5$ and $R_6$, which can be the same or different, are (i) hydrogen, wherein $R_5$ and $R_6$ are not both hydrogen; (ii) $CH(A)CO_2B$, where A is hydrogen; hydroxyl; $C_1$-$C_6$-alkyl; $C_2$-$C_6$-alkenyl; $C_2$-$C_6$-alkinyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloatkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{16}$-aryl and alkyl is $C_1$-$C_6$-alkyl; $C_8$-$C_{16}$-arylalkenyl, where aryl is $C_6$-$C_{10}$-aryl and alkenyl is $C_2$-$C_6$-alkenyl; $C_8$-$C_{16}$-arylalkinyl, where aryl is $C_6$-$C_{10}$-aryl and alkinyl is $C_2$-$C_6$-alkinyl; amino; $C_1$-$C_6$-alkylamino; and guanidino; and B is hydrogen; $C_1$-$C_{30}$ alkyl; $C_2$-$C_{30}$ alkenyl; $C_2$-$C_{30}$ alkinyl; $C_4$-$C_{16}$-cycloalkylalkyl, where cycloalkyl is $C_3$-$C_{10}$-cycloalkyl and alkyl is $C_1$-$C_6$-alkyl; $C_5$-$C_{16}$-cycloalkylalkenyl, where cycloalkyl is $C_3$-$C_{10}$-cycloalkyl and alkenyl is $C_2$-$C_6$-alkenyl; $C_5$-$C_{16}$-cycloalkylalkinyl, where cycloalkyl is $C_3$-$C_{10}$-cycloalkyl and alkinyl is $C_2$-$C_6$-alkinyl; $C_7$-$C_{16}$-arylalkyl, where aryl is $C_6$-$C_{10}$-aryl and alkyl is $C_1$-$C6$-alkyl; $C_8$-$C_{16}$-arylalkenyl, where aryl is $C_6$-$C_{16}$-aryl and alkenyl is $C_2$-$C_6$-alkenyl; $C_5$-$C_{16}$-arylalkinyl, where aryl is $C_6$-$C_{16}$-aryl and alkinyl is $C_2$-$C_6$-alkinyl; phenyl; and substituted phenyl; and (iii) $C_1$-$C_6$-alkyl-$CO_2B$, where B is hydrogen;

X is oxygen and

Y is oxygen; and pharmaceutically acceptable acid addition salts of the compound.

2. Compounds of claim 1 in which $R_1$ is $C_1$-$C_6$-alkyl; $R_2$ is $C_1$-$C_6$-alkyl or $C_7$-$C_{16}$-arylalkyl, where aryl is $C_6$-$C_{10}$-aryl and alkyl is $C_1$-$C_6$-alkyl; $R_3$, $R_4$ and $R_6$ are hydrogen; and $R_5$ is CH(A)CO$_2$B where A is hydrogen; hydroxyl; $C_1$-$C_6$-alkyl; $C_7$-$C_{16}$-arylalkyl, where aryl is $C_6$-$C_{10}$-aryl and alkyl is $C_1$-$C_6$-alkyl; amino; or guanidino; B is hydrogen or $C_1$-$C_6$-alkyl.

3. Compounds of claim 1, selected from:
(4,5α-epoxy-3-hydroxy-14β-methoxy-17-methylmorphinan-6α-ylamino)-acetic acid-tert.-butylester, (4,5α-epoxy-3-hydroxy-14β-methoxy-17-methylmorphinan-6β-ylamino)-acetic acid-tert.-butylester,
(4,5α-epoxy-3-hydroxy-14β-methoxy-17-methylmorphinan-6α-ylamino)-acetic acid, (4,5α-epoxy-3-hydroxy-14β-methoxy-17-methylmorphinan-6β-ylamino)-acetic acid,(2'S)-2'-(4,5α-epoxy-3-hydroxy-14β-methoxy-17-methylmorphinan-6α-ylamino)-propionic acid-tert.-butylester, (2'S)-2'-(4,5α-epoxy-3-hydroxy-14β-methoxy-17-methylmorphinan-6β-ylamino)-propionic acid-tert.-butylester, (2'S)-2'-(4,5α-epoxy-3-hydroxy-14β-methoxy-17-methylmorphinan-6α-ylamino)-propionic acid, (2'S)-2'-(4,5α-epoxy-3-hydroxy-14β-methoxy-17-methylmorphinan-6β-ylamino)-propionic acid, (2'S)-2'-(4,5β-epoxy-3-hydroxy-14β-methoxy-17-methylmorphinan-6α-ylamino)-3'-phenylpropionic acid-tert.-butylester, (2'S)-2'-(4,5α-epoxy-3-hydroxy-14β-methoxy-17-methylmorphinan-6β-ylamino)-3'-phenylpropionic acid-tert.-butylester, (2'S)-2'-(4,5α-epoxy-3-hydroxy-14β-methoxy-17-methylmorphinan-6α-ylamino)-3'-phenylpropionic acid, (2'S)-2'-(4,5α-epoxy-3-hydroxy-14β-methoxy-17-methylmorphinan-6β-ylamino)-3'-phenylpropionic acid, (4,5α-epoxy-3-hydroxy-14β-methoxy-17-methylmorphinan-6α-ylamino)-acetic acid-ethylester dihydrochloride, (4,5α-epoxy-3-hydroxy-14β-methoxy-17-methylmorphinan-6β-ylamino)-acetic acid-ethylester dihydrochloride, (4,5α-epoxy-3-hydroxy-14β-ethoxy-17-methylmorphinan-6α-ylamino)-acetic acid-tert.-butylester, (4,5α-epoxy-3-hydroxy-14β-ethoxy-17-methylmorphinan-6β-ylamino)-acetic acid-tert.-butylester, (4,5α-epoxy-3-hydroxy-14β-ethoxy-17-methylmorphinan-6α-ylamino)-acetic acid bis(tetrafluoroborate), (4,5α-epoxy-3-hydroxy-14β-ethoxy-17-methylmorphinan-6β-ylamino)-acetic acid bis(tetrafluoroborate), (2'S)-2'-(17-cyclopropylmethyl-4,5α-epoxy-3,14β-dihydroxymorphinan-6β-ylamino)-3-phenylpropionic acid-tert.-butylester, (2'S)-2'-(17-cyclopropylmethyl-4,5α-epoxy-3,14β-dihydroxymorphinan-6β-ylamino)-3-phenylpropionic acid bis(tetrafluoroborate), {17-cyclopropylmethyl-4,5α-epoxy-3-hydroxy-14β[(3-phenylpropyl)oxy]-morphinan-6α-ylamino}-acetic acid-tert.-butylester, {17-cyclopropylmethyl-4,5α-epoxy-3-hydroxy-14β-[(3-phenylpropyl)oxy]-morphinan-6α-ylamino}-acetic acid-tert.-butylester, (2'S)-2'-(17-cyclopropylmethyl-4,5α-epoxy-3-hydroxy-14β-[(3-phenylpropyl)oxy]-morphinan-6α-ylamino)-3-phenylpropionic acid-tert.-butylester, {17-cyclopropylmethyl-4,5α-epoxy-3-hydroxy-14β-[(3-phenylpropyl)oxy]-morphinan-6β-ylamino}-acetic acid dihydrochloride; or any pharmaceutically acceptable salt thereof.

4. A composition, comprising a compound of claim 1 or a pharmaceutically acceptable acid addition salt thereof, together with a pharmaceutically acceptable carrier substance.

5. A pharmaceutical composition comprising a compound according to claim 1 and a pharmaceutically acceptable carrier substance.

6. A method for the treatment of pain comprising administering to a subject in need an effective amount of a compound according to claim 1.

7. A compound of claim 1, wherein with respect to $R_5$ and $R_6$, (i) $C_1$-$C_{30}$-alkyl is $C_1$-$C_6$-alkyl; (ii) $C_2$-$C_{30}$-alkenyl is $C_2$-$C_6$-alkenyl; and (iii) $C_2$-$C_{30}$-alkinyl is $C_2$-$C_6$-alkinyl.

* * * * *